US010271783B2

(12) United States Patent
Yamada et al.

(10) Patent No.: US 10,271,783 B2
(45) Date of Patent: Apr. 30, 2019

(54) STIMULUS PRESENTING SYSTEM, STIMULUS PRESENTING METHOD, COMPUTER, AND CONTROL METHOD

(71) Applicant: Panasonic Corporation, Osaka (JP)

(72) Inventors: Kazunori Yamada, Aichi (JP); Kenji Mase, Aichi (JP); Junya Morita, Aichi (JP)

(73) Assignee: PANASONIC CORPORATION, Osaka (JP)

( * ) Notice: Subject to any disclaimer, the term of this patent is extended or adjusted under 35 U.S.C. 154(b) by 359 days.

(21) Appl. No.: 14/997,603

(22) Filed: Jan. 18, 2016

(65) Prior Publication Data
US 2016/0220163 A1    Aug. 4, 2016

(30) Foreign Application Priority Data

Jan. 30, 2015 (JP) ................................. 2015-017033

(51) Int. Cl.
A61B 5/00 (2006.01)
A61B 5/16 (2006.01)
(Continued)

(52) U.S. Cl.
CPC ............ A61B 5/165 (2013.01); A61B 5/0048 (2013.01); A61B 5/0476 (2013.01); A61B 5/04842 (2013.01); A61M 21/00 (2013.01); G06F 19/3481 (2013.01); G16H 20/70 (2018.01); G16H 50/20 (2018.01); A61B 5/11 (2013.01); A61B 5/1102 (2013.01);
(Continued)

(58) Field of Classification Search
CPC .......... A61B 5/16; A61B 5/165; A61B 5/486; A61B 5/7264; G09B 19/00; G09B 23/28; G09B 5/065; H04N 21/44201; H04N 21/44222
See application file for complete search history.

(56) References Cited

U.S. PATENT DOCUMENTS

2006/0293838 A1* 12/2006 Yamamoto .............. G01C 21/20
701/532
2013/0283162 A1* 10/2013 Aronsson .............. G11B 27/105
715/719
2014/0223462 A1* 8/2014 Aimone ........... H04N 21/42201
725/10

FOREIGN PATENT DOCUMENTS

JP    2006-146630    6/2006
JP    2009-199383    9/2009

* cited by examiner

Primary Examiner — Jerry-Daryl Fletcher
(74) Attorney, Agent, or Firm — Greenblum & Bernstein, P.L.C.

(57) ABSTRACT

A stimulus presenting system according to the present disclosure includes a biological information acquirer that acquires biological information on a user; a mental state estimator that estimates a mental state of the user on the basis of the biological information; a target state setter that sets a target mental state after the mental state estimator estimates that the mental state is a first mental state; a scenario creator that creates a scenario including at least one stimulus presenting content possibly influencing the mental state on the basis of the set target mental state; a content presenter that presents the stimulus presenting content on the basis of the created scenario; and a mental state determiner that determines whether a second mental state estimated by the mental state estimator on the basis of biological infor-
(Continued)

mation acquired after the presentation of the stimulus presenting content is started attains the set target mental state.

30 Claims, 16 Drawing Sheets

(51) Int. Cl.
    *A61B 5/0476*     (2006.01)
    *A61B 5/0484*     (2006.01)
    *A61M 21/00*     (2006.01)
    *G06F 19/00*     (2018.01)
    *G16H 50/20*     (2018.01)
    *G16H 20/70*     (2018.01)
    *A61B 5/11*     (2006.01)

(52) U.S. Cl.
    CPC ...... *A61B 5/6891* (2013.01); *A61M 2021/005* (2013.01); *A61M 2021/0016* (2013.01); *A61M 2021/0022* (2013.01); *A61M 2021/0027* (2013.01); *A61M 2021/0044* (2013.01); *A61M 2205/505* (2013.01); *A61M 2205/52* (2013.01); *A61M 2230/06* (2013.01); *A61M 2230/10* (2013.01); *A61M 2230/40* (2013.01); *A61M 2230/63* (2013.01)

FIG. 3

| MENTAL STATE | HEART RATE | BRAIN WAVE | BODY MOTION |
|---|---|---|---|
| RELAXATION | STABLE | MIXTURE OF LOW $\beta$ WAVE, $\theta$ WAVE, AND $\alpha$ WAVE | STABLE RHYTHM |
| CONCENTRATION | STABLE | $\alpha$ WAVE | STABLE RHYTHM |
| EXCITEMENT, SURPRISE, ACTIVENESS | LARGE VARIATION | HIGH $\beta$ WAVE | LARGE FLUCTUATION |
| JOY | MEDIUM VARIATION | LARGE POTENTIAL VARIATION | MEDIUM FLUCTUATION |
| SORROW | SMALL VARIATION | LARGE POTENTIAL VARIATION IN $\alpha$ WAVE | SMALL FLUCTUATION |

FIG. 4

| TARGET MENTAL STATE | SCENARIO (STIMULUS PRESENTING CONTENT) | |
|---|---|---|
| RELAXATION | SCENARIO A | LANDSCAPE, PICTURE FREQUENTLY VIEWED IN THE PAST |
| CONCENTRATION | SCENARIO B | BLUE-BASED UNIFORM-THEME PICTURE, FIGURE |
| EXCITEMENT, SURPRISE, ACTIVENESS | SCENARIO C | DYNAMIC COMPOSITION, PICTURE OF FRIEND |
| JOY | SCENARIO D | JOYFUL SCENE (INTENTIONAL TAGGING) |
| SORROW | SCENARIO E | SORROWFUL SCENE (INTENTIONAL TAGGING) |

STIMULUS PRESENTING SYSTEM, STIMULUS PRESENTING METHOD, COMPUTER, AND CONTROL METHOD

BACKGROUND

1. Technical Field

The present disclosure relates to a stimulus presenting system, a stimulus presenting method, a computer, and a control method that each lead the mental state of a user to a target mental state.

2. Description of the Related Art

As a stimulus presenting system, there is known a system that selects a reproduction candidate content on the basis of the mental state of a user, the environmental state, at least one piece of user attribute information, and a content selection tendency of the user (for example, see Japanese Unexamined Patent Application Publication No. 2006-146630).

As another stimulus presenting system, there is known a system that estimates the listening purpose of a sound content from a health state of a user, reproduces a target sound content, and reflects the degree of effect by the sound content into a content database (for example, see Japanese Patent No. 5184137).

SUMMARY

In one general aspect, the techniques disclosed here feature a stimulus presenting system that leads a mental state of a user to a target mental state, the system including a biological information acquirer that acquires biological information on the user; a mental state estimator that estimates the mental state of the user on the basis of the biological information acquired by the biological information acquirer; a target state setter that sets a target mental state indicative of a mental state the user aims at, after the mental state estimator estimates that the mental state of the user is a first mental state; a scenario creator that creates a scenario including at least one stimulus presenting content which may give an influence on the mental state of the user on the basis of the set target mental state; a content presenter that presents the at least one stimulus presenting content on the basis of the created scenario; and a mental state determiner that determines whether or not a second mental state which is a mental state of the user estimated by the mental state estimator on the basis of biological information on the user acquired after the presentation of the stimulus presenting content is started attains the set target mental state.

As described above, with the stimulus presenting system according to the present disclosure, the mental state of the user can be efficiently led to the target mental state.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 illustrates estimation examples of mental states of a user on the basis of biological information on the user;

FIG. 4 illustrates scenario examples of stimulus presenting contents created by a scenario creator according to the first embodiment of the present disclosure;

DETAILED DESCRIPTION

Figure 1:
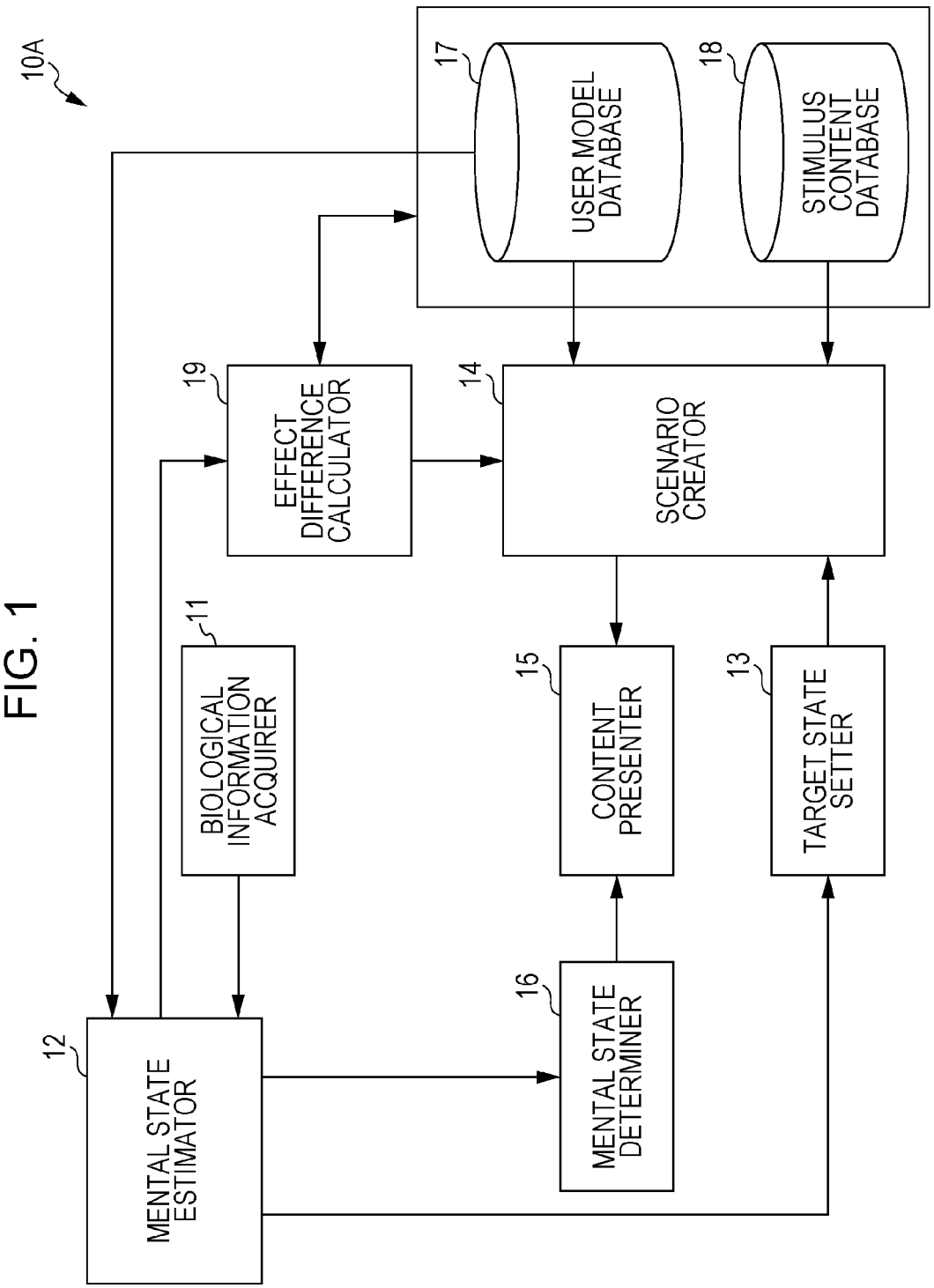
FIG. 1 is a block diagram of a configuration of a stimulus presenting system according to a first embodiment of the present disclosure.

The systems disclosed in Japanese Unexamined Patent Application Publication No. 2006-146630 and Japanese Patent No. 5184137 each have a problem in which the mental state of a user cannot be efficiently led to a target mental state.

One non-limiting and exemplary embodiment provides a stimulus presenting system, a stimulus presenting method, a computer, and a control method that can efficiently lead the mental state of a user to a target mental state.

A stimulus presenting system according to an aspect of the present disclosure is a stimulus presenting system that leads a mental state of a user to a target mental state, the system including:

a biological information acquirer that acquires biological information on the user;

a mental state estimator that estimates the mental state of the user on the basis of the biological information acquired by the biological information acquirer;

a target state setter that sets a target mental state indicative of a mental state the user aims at, after the mental state estimator estimates that the mental state of the user is a first mental state;

a scenario creator that creates a scenario including at least one stimulus presenting content which may give an influence on the mental state of the user on the basis of the set target mental state;

a content presenter that presents the at least one stimulus presenting content on the basis of the created scenario; and a mental state determiner that determines whether or not a second mental state which is a mental state of the user estimated by the mental state estimator on the basis of biological information on the user acquired after the presentation of the stimulus presenting content is started attains the set target mental state.

With this configuration, the target mental state can be set after the mental state of the user is estimated as the first mental state, and the scenario including the at least one stimulus presenting content can be created on the basis of the set target mental state. Also, in the stimulus presenting system according to the aspect of the present disclosure, it is determined whether or not the second mental state of the user changed by the stimulus presenting content attains the target mental state. Accordingly, with the stimulus presenting system according to the aspect of the present disclosure, a content can be efficiently selected and presented on the basis of a change in mental state of the user to bring the mental state of the user close to the target mental state. Therefore, the mental state of the user can be efficiently led to the target mental state.

Also, in the stimulus presenting system according to the aspect of the present disclosure, if the mental state determiner determines that the second mental state attains the target mental state, the content presenter may end the presentation of the stimulus presenting content.

With this configuration, the presentation of the stimulus presenting content can be ended at a proper time point at which the mental state of the user attains the target mental state.

Also, in the stimulus presenting system according to the aspect of the present disclosure, the target state setter may set the target mental state on the basis of input data relating to a target mental state input by an input operation by the user.

With this configuration, since the user can input the target mental state on the basis of the first mental state, the target mental state can be reliably and easily set.

Also, the stimulus presenting system according to the aspect of the present disclosure may further include:

a storage medium that stores a target mental state set in the past as history information, in which the target state setter may set the target mental state on the basis of the history information stored in the storage medium.

With this configuration, since the target mental state can be automatically set from the history information on the target mental state set in the past, the period of time required for setting the target mental state can be decreased and the target mental state can be easily set.

Also, the stimulus presenting system according to the aspect of the present disclosure may further include:

a user model database that stores a user model in which a tendency of a change in the mental state of the user caused by the presentation of the stimulus presenting content is defined in association with the user; and a stimulus content database that stores an expected change amount indicative of a change amount of the mental state of the user expected in reaction to the presentation of the stimulus presenting content, in which the scenario creator may create the scenario on the basis of at least one of data in the user model database and data in the stimulus content database.

With this configuration, the scenario for the stimulus presenting content can be customized and created for each user on the basis of the user model database. Also, the scenario creator can create a scenario so as to include a stimulus presenting content with a higher effect for changing the mental state of the user to the target mental state. Accordingly, the stimulus presenting system can efficiently lead the mental state of the user to the target mental state.

Also, the stimulus presenting system according to the aspect of the present disclosure may further include:

an effect difference calculator that calculates a difference between a first change amount indicative of a change amount of the mental state of the user caused by the presentation of the stimulus presenting content and estimated by the mental state estimator, and a second change amount indicative of a change amount of the mental state of the user caused by the presentation of the stimulus presenting content and expected on the basis of the at least one of the data in the user model database and the data in the stimulus content database, in which, if the difference calculated by the effect difference calculator is a predetermined value or larger, the scenario creator may change the scenario.

With this configuration, the difference between the first change amount of the mental state of the user caused by the actually presented stimulus presenting content, and the expected second change amount of the mental state of the user can be calculated. Accordingly, the scenario creator can change the scenario to include a stimulus presenting content with a higher effect for leading the mental state of the user to the target mental state. As described above, with the stimulus presenting system according to the aspect of the present disclosure, the scenario for the stimulus presenting content can be optimized in real time, and hence the mental state of the user can be efficiently led to the target mental state.

Also, in the stimulus presenting system according to the aspect of the present disclosure, if the difference is the predetermined value or larger, the effect difference calculator may update the at least one of the data in the user model database and the data in the stimulus content database.

With this configuration, if the change amount of the mental state of the user caused by the actually presented stimulus presenting content is different from the expected change amount, the at least one of the data in the user model database and the data in the stimulus content database can be updated. Accordingly, the stimulus presenting system can efficiently lead the mental state of the user to the target mental state.

Also, the stimulus presenting system according to the aspect of the present disclosure may further include:

a concentration judger that judges whether or not the user concentrates on the stimulus presenting content if the difference calculated by the effect difference calculator is the predetermined value or larger, in which, if the concentration judger judges that the user does not concentrate on the stimulus presenting content, the difference calculated by the effect difference calculator may be corrected.

With this configuration, if the user does not concentrate on the stimulus presenting content, by correcting the difference calculated by the effect difference calculator, the result of the effect by the stimulus presenting content presented while the user does not concentrate can be eliminated. Accordingly, in the stimulus presenting system, since the data on the effect by the stimulus presenting content for the user can be correctly collected, the mental state of the user can be further efficiently led to the target mental state.

Also, in the stimulus presenting system according to the aspect of the present disclosure, the biological information acquired by the biological information acquirer may include brain activity information indicative of an activity state of the brain of the user and biological information other than the brain activity information, the content presenter may further present a concentration judging content to judge whether or not the user concentrates on the stimulus presenting content, and the concentration judger may judge whether or not the user concentrates on the stimulus presenting content on the basis of at least one of the brain activity information and the biological information other than the brain activity information acquired by the biological information acquirer after the presentation of the concentration judging content.

With this configuration, since the concentration judgment for the user can be executed on the basis of the biological information, it can be easily judged whether or not the user concentrates on the stimulus presenting content.

Also, in the stimulus presenting system according to the aspect of the present disclosure, the concentration judger may compare first brain activity information included in biological information acquired in a period after the presentation of the concentration judging content and before presentation of a next content with second brain activity information included in biological information acquired during presentation of a stimulus presenting content other than the concentration judging content, judge that the user concentrates if a difference between the first brain activity information and the second brain activity information is a predetermined amount or more, and judge that the user does not concentrate otherwise.

With this configuration, it can be further reliably judged whether or not the user concentrates on the content presented by the content presenter.

Also, in the stimulus presenting system according to the aspect of the present disclosure, the stimulus content database may hold attribute information in which the stimulus presenting content is classified on the basis of at least one of a type of content and an effect given to the mental state of the user, the scenario creator may create a scenario including the stimulus presenting content and the concentration judging content on the basis of the attribute information held in the stimulus content database, and the concentration judging content may include a content having attribute information different from the attribute information on the stimulus presenting content.

With this configuration, since the concentration judging content markedly different from the stimulus presenting content can be presented to the user, it can be further reliably judged whether or not the user concentrates on the content.

Also, in the stimulus presenting system according to the aspect of the present disclosure, the scenario creator may create a scenario that presents the concentration judging content with a lower frequency than a frequency with which the stimulus presenting content is presented.

With this configuration, it can be further reliably judged whether or not the user concentrates on the presented content.

Also, in the stimulus presenting system according to the aspect of the present disclosure, the scenario creator may judge the number of pieces of attribute information being the same as at least one piece of attribute information owned by a content presented previously to the presentation of the concentration judging content and a similarity of attribute information on the basis of the attribute information held in the stimulus content database, and select a content with the lowest similarity as the concentration judging content.

With this configuration, it can be further reliably judged whether or not the user concentrates on the presented content.

Also, in the stimulus presenting system according to the aspect of the present disclosure, if the concentration judger judges that the user does not concentrate on the stimulus presenting content, the content presenter may generate a sound.

With this configuration, attention can be drawn with the sound if the user does not concentrate on the content, and hence the user can concentrate on the content.

Also, in the stimulus presenting system according to the aspect of the present disclosure, at least one of the mental state estimator, the scenario creator, and the mental state determiner may include a processor.

A stimulus presenting method according to another aspect of the present disclosure is a stimulus presenting method that leads a mental state of a user to a target mental state, the method including:

acquiring biological information on the user;

estimating the mental state of the user on the basis of the biological information;

setting a target mental state indicative of a mental state the user aims at, after it is estimated that the mental state of the user is a first mental state;

creating a scenario including at least one stimulus presenting content which may give an influence on the mental state of the user on the basis of the set target mental state;

presenting the at least one stimulus presenting content on the basis of the created scenario; and determining whether or not a second mental state which is an estimated mental state of the user on the basis of biological information on the user acquired after the presentation of the stimulus presenting content is started attains the target mental state.

With this configuration, the target mental state can be set on the basis of the first mental state estimated with the biological information on the user, and the scenario for the stimulus presenting content can be created on the basis of the set target state. Also, with the stimulus presenting method according to the aspect of the present disclosure, since it is determined whether or not the second mental state of the user, which is changed by the stimulus presenting content, attains the target mental state, the mental state of the user can be efficiently led to the target mental state.

Also, in the stimulus presenting method according to the aspect of the present disclosure, if the mental state determination determines that the second mental state attains the target mental state, the presentation of the stimulus presenting content may be ended.

With this configuration, the presentation of the stimulus presenting content can be ended at a proper time point at which the mental state of the user attains the target mental state.

Also, in the stimulus presenting method according to the aspect of the present disclosure, the target state setting may include setting the target mental state on the basis of input data relating to a target mental state input by an input operation by the user.

With this configuration, since the user can input the target mental state, the target mental state can be reliably and easily set.

Also, in the stimulus presenting method according to the aspect of the present disclosure, the target state setting may set the target mental state on the basis of history information on a target mental state set in the past and stored in a storage medium.

With this configuration, since the target mental state can be automatically set from the history information on the target mental state set in the past, the period of time required for setting the target mental state can be decreased and the target mental state can be easily set.

Also, in the stimulus presenting method according to the aspect of the present disclosure, the scenario creation may further create the scenario on the basis of at least one of data in a user model database that stores a user model in which a tendency of a change in the mental state of the user caused by the presentation of the stimulus presenting content is defined in association with the user, and data in a stimulus content database that stores an expected change amount indicative of a change amount of the mental state of the user expected in reaction to the presentation of the stimulus presenting content.

With this configuration, the scenario for the stimulus presenting content can be customized and created in association with the user on the basis of the user model database. Also, the scenario can be created to include a stimulus presenting content with a higher effect for changing the mental state of the user to the target mental state. Accordingly, with the stimulus presenting method, the mental state of the user can be further efficiently led to the target mental state.

Also, the stimulus presenting method according to the aspect of the present disclosure, may further include:

calculating a difference between a first change amount indicative of a change amount of the mental state of the user caused by the presentation of the stimulus presenting content and estimated in the mental state estimation, and a second change amount indicative of a change amount of the mental state of the user caused by the presentation of the stimulus presenting content and expected on the basis of the at least one of the data in the user model database and the data in the stimulus content database; and changing the scenario if the difference calculated in the effect difference calculation is a predetermined value or larger.

With this configuration, the difference between the first change amount of the mental state of the user caused by the actually presented stimulus presenting content, and the expected second change amount of the mental state of the user can be calculated. Accordingly, with the stimulus presenting method according to the aspect of the present disclosure, the scenario for presenting the stimulus presenting content can be changed to include a stimulus presenting content with a higher effect for leading the mental state of the user to the target mental state. As described above, with the stimulus presenting method according to the aspect of the present disclosure, the scenario for the stimulus presenting content can be optimized in real time, and hence the mental state of the user can be efficiently led to the target mental state.

Also, the stimulus presenting method according to the aspect of the present disclosure, may further include updating the at least one of the data in the user model database and the data in the stimulus content database if the difference calculated in the effect difference calculation is the predetermined value or larger.

With this configuration, if the change amount of the mental state of the user caused by the actually presented stimulus presenting content is different from the expected change amount, the at least one of the data in the user model database and the data in the stimulus content database can be updated. Accordingly, with the stimulus presenting method according to the aspect of the present disclosure, the mental state of the user can be further efficiently led to the target mental state.

Also, the stimulus presenting method according to the aspect of the present disclosure, may further include:

judging whether or not the user concentrates on the stimulus presenting content if the difference calculated in the effect difference calculation is the predetermined value or larger, in which, if the concentration judgment judges that the user does not concentrate on the stimulus presenting content, the concentration judgment may include correcting the difference calculated in the effect difference calculation.

With this configuration, if the user does not concentrate on the stimulus presenting content, by correcting the difference calculated in the effect difference calculation, the result of the effect by the stimulus presenting content presented while the user does not concentrate can be eliminated. Accordingly, with the stimulus presenting method, since the data on the effect by the stimulus presenting content for the user can be correctly collected, the mental state of the user can be further efficiently led to the target mental state.

Also, in the stimulus presenting method according to the aspect of the present disclosure, the biological information acquired in the biological information acquisition may include brain activity information indicative of an activity state of the brain of the user and biological information other than the brain activity information, the content presentation may further present a concentration judging content to judge whether or not the user concentrates on the stimulus presenting content, and the concentration judgment may judge whether or not the user concentrates on the stimulus presenting content on the basis of at least one of the brain activity information and the biological information other than the brain activity information acquired in the biological information acquisition after the presentation of the concentration judging content.

With this configuration, since the concentration judgment for the user can be executed on the basis of the biological information, it can be easily judged whether or not the user concentrates on the stimulus presenting content.

Also, in the stimulus presenting method according to the aspect of the present disclosure, the concentration judgment may compare first brain activity information included in biological information acquired in a period after the presentation of the concentration judging content and before presentation of a next stimulus presenting content with second brain activity information included in biological information acquired during presentation of a content other than the concentration judging content, judge that the user concentrates if a difference between the first brain activity information and the second brain activity information is a predetermined amount or more, and judge that the user does not concentrate otherwise.

With this configuration, it can be further reliably judged whether or not the user concentrates on the presented content.

Also, the stimulus presenting method according to the aspect of the present disclosure may further include:

changing the scenario created in the scenario creation into a scenario including the stimulus presenting content and the concentration judging content on the basis of attribute information in which the stimulus presenting content held in the stimulus content database is classified on the basis of at least one of a type of content and an effect given to the mental state of the user, in which the concentration judging content may include a content having attribute information different from the attribute information on the stimulus presenting content.

With this configuration, since the concentration judging content markedly different from the stimulus presenting content can be presented to the user, it can be further reliably judged whether or not the user concentrates on the presented content.

Also, in the stimulus presenting method according to the aspect of the present disclosure, the scenario changing may change the scenario to a scenario that presents the concentration judging content with a lower frequency than a frequency with which the stimulus presenting content is presented.

With this configuration, it can be further reliably judged whether or not the user concentrates on the presented content.

Also, in the stimulus presenting method according to the aspect of the present disclosure, the scenario changing may judge the number of pieces of attribute information being the same as at least one piece of attribute information owned by a content presented previously to the presentation of the concentration judging content and a similarity of attribute information on the basis of the attribute information held in the stimulus content database, and select a content with the lowest similarity as the concentration judging content.

With this configuration, it can be further reliably judged whether or not the user concentrates on the presented content.

Also, the stimulus presenting method according to the aspect of the present disclosure may further include generating a sound if the concentration judgment judges that the user does not concentrate on the stimulus presenting content.

With this configuration, attention can be drawn with the sound if the user does not concentrate on the content, and hence the user can concentrate on the content.

Also, in the stimulus presenting method according to the aspect of the present disclosure, at least one of the mental state estimation, the scenario creation, and the mental state determination may be executed by a processor included in a stimulus presenting system.

A computer according to still another aspect of the present disclosure is a computer included in a stimulus presenting system that leads a mental state of a user to a target mental state, the computer including:

a mental state estimator that estimates the mental state of the user on the basis of biological information acquired by a biological information acquiring device connected to the computer;

a scenario creator that creates a scenario including at least one stimulus presenting content which may give an influence on the mental state of the user on the basis of a target mental state indicative of a mental state the user aims at set by a target state setting device connected to the computer after the mental state estimator estimates that the mental state of the user is a first mental state, and transmits the created scenario to a content presenting device connected to the computer; and a mental state determiner that determines whether or not a second mental state which is a mental state of the user estimated by the mental state estimator on the basis of biological information on the user acquired after the presentation of the stimulus presenting content by the content presenting device is started attains the set target mental state.

With this configuration, after the mental state of the user is estimated as the first mental state, the scenario including the at least one stimulus presenting content can be created on the basis of the set target mental state. Also, with the computer according to the aspect of the present disclosure, it is determined whether or not the second mental state of the user changed by the stimulus presenting content attains the target mental state. Accordingly, with the computer according to the aspect of the present disclosure, the content can be efficiently selected on the basis of the change in mental state of the user, and the content can be efficiently presented by the content presenting device, to bring the mental state of the user close to the target mental state. Accordingly, the mental state of the user can be efficiently led to the target mental state.

Also, in the computer according to the aspect of the present disclosure, at least one of the mental state estimator, the scenario creator, and the mental state determiner may include a processor.

A control method of a computer according to yet another aspect of the present disclosure is a control method of a computer included in a stimulus presenting system that leads a mental state of a user to a target mental state, the method including:

estimating the mental state of the user on the basis of biological information acquired by a biological information acquiring device connected to the computer;

creating a scenario including at least one stimulus presenting content which may give an influence on the mental state of the user on the basis of a target mental state indicative of a mental state the user aims at set by a target state setting device connected to the computer after the mental state estimation estimates that the mental state of the user is a first mental state, and transmits the created scenario to a content presenting device connected to the computer; and determining whether or not a second mental state which is a mental state of the user estimated in the mental state estimation on the basis of biological information on the user acquired after the presentation of the stimulus presenting content by the content presenting device is started attains the set target mental state.

With this configuration, after the mental state of the user is estimated as the first mental state, the scenario including the at least one stimulus presenting content can be created on the basis of the set target mental state. Also, with the control method of the computer according to the aspect of the present disclosure, it is determined whether or not the second mental state of the user changed by the stimulus presenting content attains the target mental state. Accordingly, with the control method of the computer according to the aspect of the present disclosure, the content can be efficiently selected on the basis of the change in mental state of the user, and the content can be efficiently presented by the content presenting device, to bring the mental state of the user close to the target mental state. Accordingly, the mental state of the user can be efficiently led to the target mental state.

Also, in the control method according to the aspect of the present disclosure, at least one of the mental state estimation, the scenario creation, and the mental state determination may be executed by a processor.

Embodiments of the present disclosure are described below with reference to the accompanying drawings. Also, in the respective drawings, respective elements are exaggeratedly illustrated for easily understanding the description.

First Embodiment

General Configuration

FIG. 1 is a block diagram of a configuration of a stimulus presenting system 10A according to a first embodiment. As shown in FIG. 1, the stimulus presenting system 10A includes a biological information acquirer 11, a mental state estimator 12, a target state setter 13, a scenario creator 14, a content presenter 15, a mental state determiner 16, a user model database 17, a stimulus content database 18, and an effect difference calculator 19. Also, the stimulus presenting system 10A is configured with a computer mounted thereon. These components are controlled by the computer.

The computer of the stimulus presenting system 10A includes, for example, a processing circuit (not shown) such as a central processing unit (CPU), and a storage medium. The storage medium is a readable storage medium or a readable/writable storage medium (a first storage medium). For example, the storage medium is a hard disk (not shown) or a memory (not shown).

The first storage medium stores, for example, respective programs that cause the computer to function as the mental state estimator 12, the scenario creator 14, the mental state determiner 16, and the effect difference calculator 19.

Also, the first storage medium stores, for example, respective programs that control the biological information acquirer 11, the content presenter 15, and the target state setter 13.

Also, the first storage medium stores programs that make accesses (reading, writing, etc.) to the user model database 17 and the stimulus content database 18.

When the processing circuit of the computer executes these programs stored in the first storage medium, the computer causes the mental state estimator 12, the scenario creator 14, the mental state determiner 16, and the effect difference calculator 19 to function, controls the biological information acquirer 11, the content presenter 15, and the target state setter 13, and makes accesses to the user model database 17 and the stimulus content database 18.

For example, the above-described programs may be previously stored in the first storage medium. Alternatively, the above-described programs may be downloaded from a server apparatus (not shown) that stores the programs through a communication line such as the Internet (not shown), and the downloaded programs may be stored in the first storage medium. In this case, the first storage medium is desirably a readable and writable storage medium.

Alternatively, the computer of the stimulus presenting system 10A may be provided by using an integrated circuit incorporating the functions and operations to be provided by executing the programs stored in the above-described first storage medium with the processing circuit.

It is to be noted that the biological information acquirer 11, the target state setter 13, and the content presenter 15 may be also referred to as a biological information acquiring device 11, a target state setting device 13, and a content presenting device 15, respectively.

The biological information acquirer 11, the target state setter 13, and the content presenter 15 may be physically integrally configured with the computer of the stimulus presenting system 10A.

Also, the computer may include, for example, a readable and writable storage medium (a second storage medium).

The second storage medium is a readable and writable storage medium, and is, for example, a hard disk (not shown) or a memory.

The second storage medium stores, for example, information relating to the user model database 17 and information relating to the stimulus content database 18.

The computer includes the second storage medium as described above; however, it is not limited thereto. For example, the second storage medium may be physically independent from the computer and may be connected to the computer. This connection may be, for example, wired connection or wireless connection using wireless communication.

It is to be noted that "stimulus presentation" represents presentation of a stimulus that may possibly give an influence on the mental state of a user (for example, sense organs of sight, hearing, smell, touch, and taste, and in higher order, various stimuli such as a stimulus to the brain).

Figure 2:
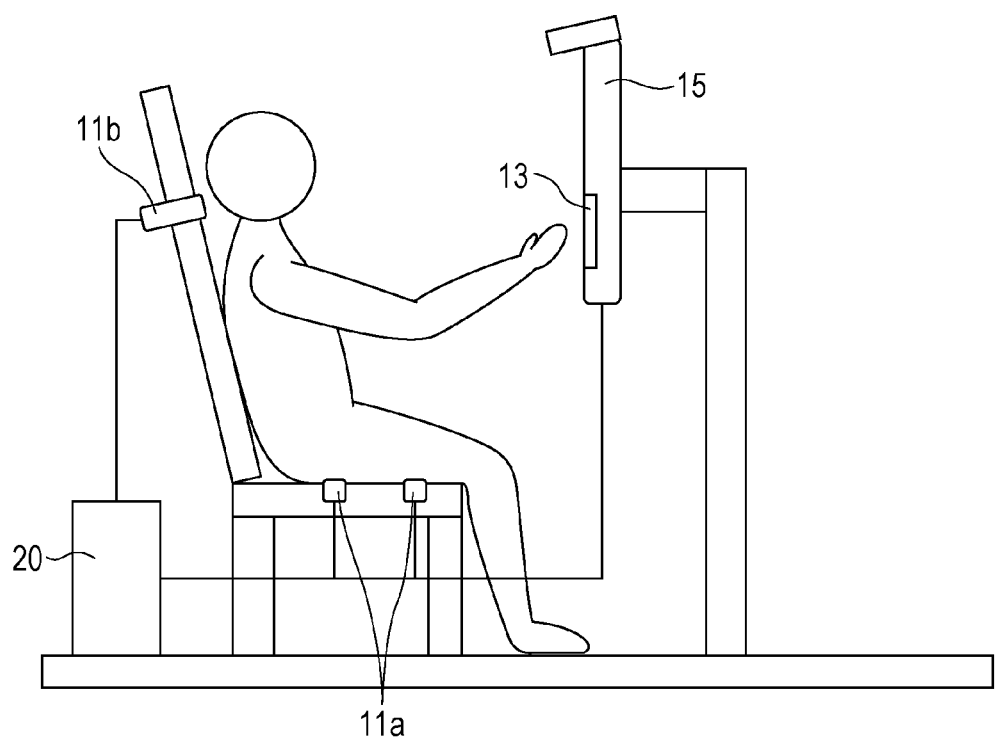
FIG. 2 illustrates an application example of the stimulus presenting system according to the first embodiment of the present disclosure.

FIG. 2 is a schematic illustration showing an application example of the stimulus presenting system 10A according to the first embodiment of the present disclosure. As shown in FIG. 2, the stimulus presenting system 10A is applied to a chair. The chair with the stimulus presenting system 10A applied includes biological information acquirers 11a and 11b respectively in a lower section of a seat of the chair and a backrest section of the chair. The biological information acquirers 11a and 11b acquire biological information on a user. Also, the target state setter 13 that sets a target mental state of the user, and the content presenter 15 that presents a content to the user are provided in front of the chair. The biological information acquirers 11a and 11b, the target state setter 13, and the content presenter 15 are connected to a computer 20.

The computer 20 is described as a computer including, for example, the mental state estimator 12, the scenario creator 14, the mental state determiner 16, the user model database 17, the stimulus content database 18, and the effect difference calculator 19.

Also, the computer 20 does not have to be attached to the chair, and may be arranged at a position different from the position at which the chair is arranged. For example, the computer 20 may be a server apparatus (not shown) connected to the chair through a network.

A detailed configuration of the stimulus presenting system 10A is described.

Biological Information Acquirer

The biological information acquirer 11 is a sensor that acquires biological information on the user. The biological information is information on, for example, the heart rate, respiration, brain wave (electroencephalograpy (EEG) signal), brain magnetic field (magnetoencephalography (MEG) signal), oxygen density, bloodstream, facial expression, body motion, etc., of the user. The biological information acquirer 11 may include, for example, at least one sensor that acquires the biological information on the user. The biological information acquirer 11 according to the first embodiment includes a pressure sensor 11a that acquires the heart rate and body motion (first biological information) of the user, and a sensor that acquires brain activity information (second biological information) of the user. The brain activity information is information including an activity state of the brain. The sensor that acquires the brain activity information may be, for example, an electric potential sensor or a magnetic sensor. For example, an electric potential sensor is attached to a head portion of the user, and brain activity information (brain wave information) is acquired by using information (an electric potential) detected by the electric potential sensor. For example, a magnetic sensor is attached to a head portion of the user, and brain activity information (brain magnetic field information) is acquired by using information (a magnetic field) detected by the magnetic sensor. In the drawing, as the sensor that acquires the brain activity information on the user, the biological information acquirer 11 includes, for example, a brain wave sensor 11$b$ corresponding to the electric potential sensor that acquires brain wave information. As shown in FIG. 2, the pressure sensor 11$a$ is arranged in the lower section of the seat of the chair. The brain wave sensor 11$b$ is arranged in the backrest section of the chair. The biological information acquirer 11 acquires the biological information on the user in real time. In this embodiment, the biological information includes the first biological information and the second biological information. Data on the biological information acquired by the biological information acquirer 11 is transmitted to the mental state estimator 12.

Mental State Estimator

The mental state estimator 12 estimates the mental state of the user on the basis of the biological information on the user acquired by the biological information acquirer 11. The mental state of the user is a mental state, such as relaxation, concentration, excitement, surprise, activeness, joy, and sorrow. In the first embodiment, the mental state estimator 12 estimates the mental state of the user by using the heart rate and body motion acquired by the pressure sensor 11$a$, and the brain wave acquired by the brain wave sensor 11$b$. The mental state estimator 12 can estimate the mental state of the user in real time on the basis of the biological information acquirer 11.

The mental state estimator 12 estimates the mental state of the user before presentation of a stimulus presenting content on the basis of biological information acquired by the biological information acquirer 11 before the presentation of the stimulus presenting content.

Also, the mental state estimator 12 estimates the mental state of the user after the presentation of the stimulus presenting content is started on the basis of biological information acquired by the biological information acquirer 11 after the presentation of the stimulus presenting content is started.

The time point after the presentation of the stimulus presenting content is started includes, for example, a time point immediately after the presentation of the stimulus presenting content is started, a time point during the presentation of the stimulus presenting content, a time point in a period from when the presentation of the stimulus presenting content is ended to when presentation of a next stimulus presenting content is started (also referred to as a time point after the presentation of the stimulus presenting content is ended).

That is, the mental state estimator 12 estimates the mental state of the user on the basis of the biological information acquired by the biological information acquirer 11, for example, at the time point immediately after the presentation of the stimulus presenting content is started, the time point during the presentation of the stimulus presenting content, and the time point after the presentation of the stimulus presenting content is ended. In the first embodiment, the mental state estimator 12 particularly estimates the mental state before the presentation of the stimulus presenting content, the mental state during the presentation of the stimulus presenting content, and the mental state after the presentation of the stimulus presenting content.

Data on these mental states of the user estimated by the mental state estimator 12 is transmitted to the target state setter 13 and the mental state determiner 16. Also, the mental state estimator 12 is connected to the user model database 17 (described later), and receives information on each user (a user model) from the user model database 17. The user model database 17 is database that stores a user who uses the stimulus presenting system 10A and information relating to this user. That is, the mental state estimator 12 estimates the mental state of the user on the basis of the user model in the user model database 17.

A method of estimating the mental state of a user on the basis of biological information is described.

As the method of estimating the mental state, for example, there is studied an estimating method using statistical mechanical learning from the heart rate. When data on biological information acquired by the system of the present disclosure is used, for example, a stable state may be observed in a relaxed state according to R-R interval (RRI) which is variability time-series data on the heart rate, and also a mixture of an α wave, a low β wave, and a θ wave as a brain wave. Also, regarding the body motion, a stable rhythm with 3 Hz or lower is measured. Also, regarding the heart rate, by using balance of low frequency/high frequency (LF/HF) of RRI, the tension state of parasympathetic nerves can be estimated. With this estimating method, characteristic amounts of RRI etc. are extracted from the signals of the heart rate, body motion, and brain wave obtained from the plurality of sensors; statistical processing, such as pattern recognition or regression analysis, is executed on the characteristic amounts; and hence the state can be estimated as relaxed state. Similarly, mental states, such as concentration, excitement, joy, and sorrow, can be estimated by learning with statistical processing using the characteristic amounts of the aforementioned mental states.

FIG. 3 illustrates estimation examples of mental states of a user on the basis of biological information on the user. As shown in FIG. 3, for the mental state of the user, for example, "relaxation," "concentration," "excitement, surprise, activeness," "joy," and "sorrow" are defined. For example, if the heart rate of the user is stable, the low β wave, θ wave, and α wave are present in a mixed manner, and the rhythm of the body motion is stable, the mental state estimator 12 estimates that the mental state of the user is "relaxation." Also, if the heart rate of the user is largely varied, the high β wave is present, and the body motion is largely fluctuated, the mental state estimator 12 estimates that the mental state of the user is "excitement, surprise, activeness." As described above, the mental state estimator 12 estimates the mental state of the user from among "relaxation," "concentration," "excitement, surprise, activeness," "joy," and "sorrow" on the basis of the biological information on the heart rate, brain wave, and body motion of the user shown in FIG. 3.

Target State Setter

The target state setter 13 sets a target mental state indicative of a mental state the user aims at. The target state setter 13 includes a display section that displays the mental state of the user, and an input operation section to which the user executes an input operation. The display section displays the current mental state of the user estimated by the mental state estimator 12. The user inputs a target mental state to the input operation section on the basis of the mental state of the user displayed on the display section. As the target state setter 13, for example, a touch panel may be used. With the target state setter 13, for example, the user recognizes that the current mental state displayed on a display panel corresponding to the display section is "sorrow," and then inputs "joy" by operating a touch panel corresponding to the input operation section. Accordingly, the user can set the target mental state to "joy." Data on the target mental state set by the target state setter 13 is transmitted to the scenario creator 14.

Scenario Creator

The scenario creator 14 creates a scenario for a stimulus presenting content on the basis of the target mental state set by the target state setter 13. The stimulus presenting content is a content that may give an influence on the mental state of the user. In this embodiment, an example of a stimulus presenting content including at least one of video or sound is described. The video includes, for example, a picture, a still image of a figure etc., and a movie. The sound includes, for example, music and radio. The scenario may be the order of presentation, the period of presentation, the number of times of presentation, etc., of a single or a plurality of stimulus presenting contents.

In addition, if a content that moves in a screen of the display section of the content presenter 15, for example, a slideshow with pictures or the like is presented, the scenario includes a presentation position of pictures or the like to be presented and a motion within the screen during presentation. Data on the scenario created by the scenario creator 14 is transmitted to the content presenter 15.

In scenario creation, to determine the content display order corresponding to each of at least one stimulus presenting content, the priority order of each of content candidates when a content to be displayed next is selected can be determined on the basis of an inter-content similarity held in the stimulus content database 18. Accordingly, since the content is presented according to a network formed on the basis of the inter-content similarity, a scenario having more natural transaction for the user can be created. The network of similarity is a logical network, and can be drawn like FIG. 9. In particular, the similarity can be judged from the relationship of connection for each characteristic owned by the contents. Also, if a scenario for the purpose of providing surprise is created, a content can be selected so as to present a content deviated from the network of the inter-content similarity.

At this time, the inter-content similarity may be measured by the number of co-occurrence times based on a recognition model of a characteristic, such as a subject included in the content, a composition, contrast, etc. Accordingly, an initial value of an inter-content similarity for an individual can be obtained. Further, by acquiring a biological signal (concentration, stability, surprise) during content presentation, the inter-content similarity can be adjusted.

Also, by previously determining a similarity of attribute information itself of a content such that the similarity between joy and sorrow is low but the similarity between joy and excitement is high for, the previously determined similarity can serve as a reference for judging the similarity of the content itself.

An example is described in which the scenario creator 14 creates a scenario according to the first embodiment.

FIG. 4 is scenario examples of stimulus presenting contents created by the scenario creator 14. As shown in FIG. 4, if the target mental state is "relaxation," the scenario creator 14 creates a scenario A for at least one stimulus presenting content expected to attain an effect of "relaxation." The stimulus presenting content expected to attain the effect of "relaxation" included in the scenario A includes, for example, one of "landscape" and "picture frequently viewed in the past."

Also, if the target mental state is "concentration," the scenario creator 14 creates a scenario B of at least one stimulus presenting content expected to attain an effect of "concentration." The stimulus presenting content expected to attain the effect of "concentration" included in the scenario B includes, for example, "blue-based uniform-theme picture, figure."

Also, if the target mental state is "excitement, surprise, activeness," the scenario creator 14 creates a scenario C of at least one stimulus presenting content expected to attain an effect of such a mental state. A stimulus presenting content expected to attain the effect of "excitement, surprise, activeness" included in the scenario C includes, for example, one of "dynamic composition" and "picture of friend."

Also, if the target mental state is "joy," the scenario creator 14 creates a scenario D of at least one stimulus presenting content expected to attain an effect of "joy." The stimulus presenting content expected to attain the effect of "joy" included in the scenario D includes, for example, "joyful scene."

Also, if the target mental state is "sorrow," the scenario creator 14 creates a scenario E of at least one stimulus presenting content expected to attain an effect of "sorrow." The stimulus presenting content expected to attain the effect of "sorrow" included in the scenario E includes, for example, "sorrowful scene."

The scenario creator 14 selects a stimulus presenting content having a higher effect to lead the user to the target mental state on the basis of the user model database 17 (described later) and the stimulus content database 18 (described later) from contents held in the stimulus content database 18, and creates a scenario.

Figure 5:
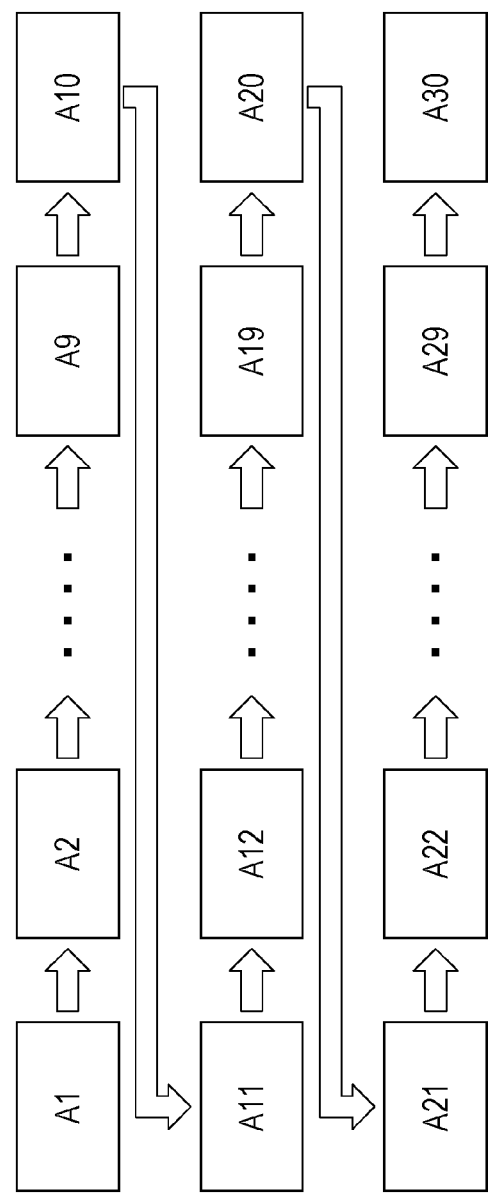
FIG. 5 illustrates a presentation example of stimulus presenting contents on the basis of a scenario created by the scenario creator according to the first embodiment of the present disclosure.

FIG. 5 illustrates a presentation example of stimulus presenting contents based on the scenario A created by the scenario creator 14. As shown in FIG. 5, the scenario A for leading the mental state of the user to "relaxation" is created so as to present stimulus presenting contents A1 to A30 mainly including landscapes or pictures frequently viewed in the past, in that order at a predetermined time interval (for example, an interval of 10 seconds).

Content Presenter

The content presenter 15 presents at least one stimulus presenting content on the basis of a scenario created by the scenario creator 14. The content presenter 15 includes a display section that displays video and a loudspeaker that reproduces sound. The content presenter 15 presents, for example, a stimulus presenting content on the basis of one of the scenarios A to E shown in FIG. 4. The content presenter 15 presents, for example, the stimulus presenting contents A1 to A30 based on the scenario A shown in FIG. 5 from the display and the loudspeaker.

Mental State Determiner

The mental state determiner 16 determines whether or not the mental state of a user changed by a stimulus presenting content presented by the content presenter 15 attains a target mental state. To be specific, the mental state determiner 16 determines whether or not the mental state of the user estimated by the mental state estimator 12 attains the target mental state during presentation of the stimulus presenting content or after the presentation of the stimulus presenting content. The time point after the presentation of the stimulus presenting content is, for example, a time point after the presentation of the stimulus presenting content is started or a time point after the presentation of the stimulus presenting content is ended. If the mental state determiner 16 determines that the mental state of the user attains the target mental state, the mental state determiner 16 ends the presentation of the stimulus presenting content from the content presenter 15. In contrast, if the mental state determiner 16 determines that the mental state of the user does not attain the target mental state, the mental state determiner 16 continues the presentation of the stimulus presenting content from the content presenter 15.

User Model Database

The user model database 17 stores a user model in which a tendency of a change in mental state of a user caused by presentation of a stimulus presenting content is defined for each user. In the user model, a difference in effect applied to a mental state by a stimulus presenting content is defined in association with a user. Also, in a case in which a plurality of users use the stimulus presenting system 10A, a user model may be defined for each user. Accordingly, a difference in effect applied to the mental state of an individual user can be defined even with the same stimulus presenting content.

For example, there may be a user who is relaxed and a user who is excited when viewing pictures of mountains. Also, even when users view a picture of the same mountain, the degree of change in mental state may vary depending on the users. Hence, if a scenario for a stimulus presenting content to be presented to a user is customized to be suitable for each user, the mental state of the user can be efficiently led to the target mental state. The user model database 17 stores a user model in which a relationship between a stimulus presenting content and an effect applied by the stimulus presenting content to the mental state are defined in association with a user. Also, when a plurality of users use the stimulus presenting system 10A, the user model database 17 stores a user model for each user.

In the first embodiment, information on a user model stored in the user model database 17 is used when the scenario creator 14 creates a scenario for a stimulus presenting content. Also, the user model stored in the user model database 17 is updated on the basis of a difference between an effect of a presented stimulus presenting content and an effect expected with the user model calculated by the effect difference calculator 19 (described later). Also, the user model database 17 is connected to the mental state estimator 12, and provides data on the user model to the mental state estimator 12.

Stimulus Content Database

The stimulus content database 18 stores an expected change amount indicative of a change amount of the mental state of a user expected in reaction to presentation of a stimulus presenting content. The expected change amount of the mental state of the user caused by the stimulus presenting content is an expected change amount of the mental state of the user before and after presentation of a certain stimulus presenting content. The time point after the presentation of the stimulus presenting content is, for example, a time point before the presentation of the content is started, a time point during the presentation of the content, or a time point after the presentation of the content is ended. The stimulus content database 18 stores a relationship between a stimulus presenting content and an expected change amount of the mental state of a user applied by the stimulus presenting content. To be specific, the stimulus content database 18 stores attribute information on a stimulus presenting content. On the basis of the attribute information, the stimulus content database 18 determines an expected change amount of the mental state of a user caused by the stimulus presenting content. The attribute information is information indicating the most effective one of a plurality of target mental states when led by a stimulus presenting content. In the first embodiment, the attribute information is created so that stimulus presenting contents are classified on the basis of the type of content and the effect to be applied to the mental state of the user. In the first embodiment, data in the stimulus content database 18 is used when the scenario creator 14 creates a scenario for a stimulus presenting content.

The attribute information is described in detail with reference to FIG. 6.

Figure 6:
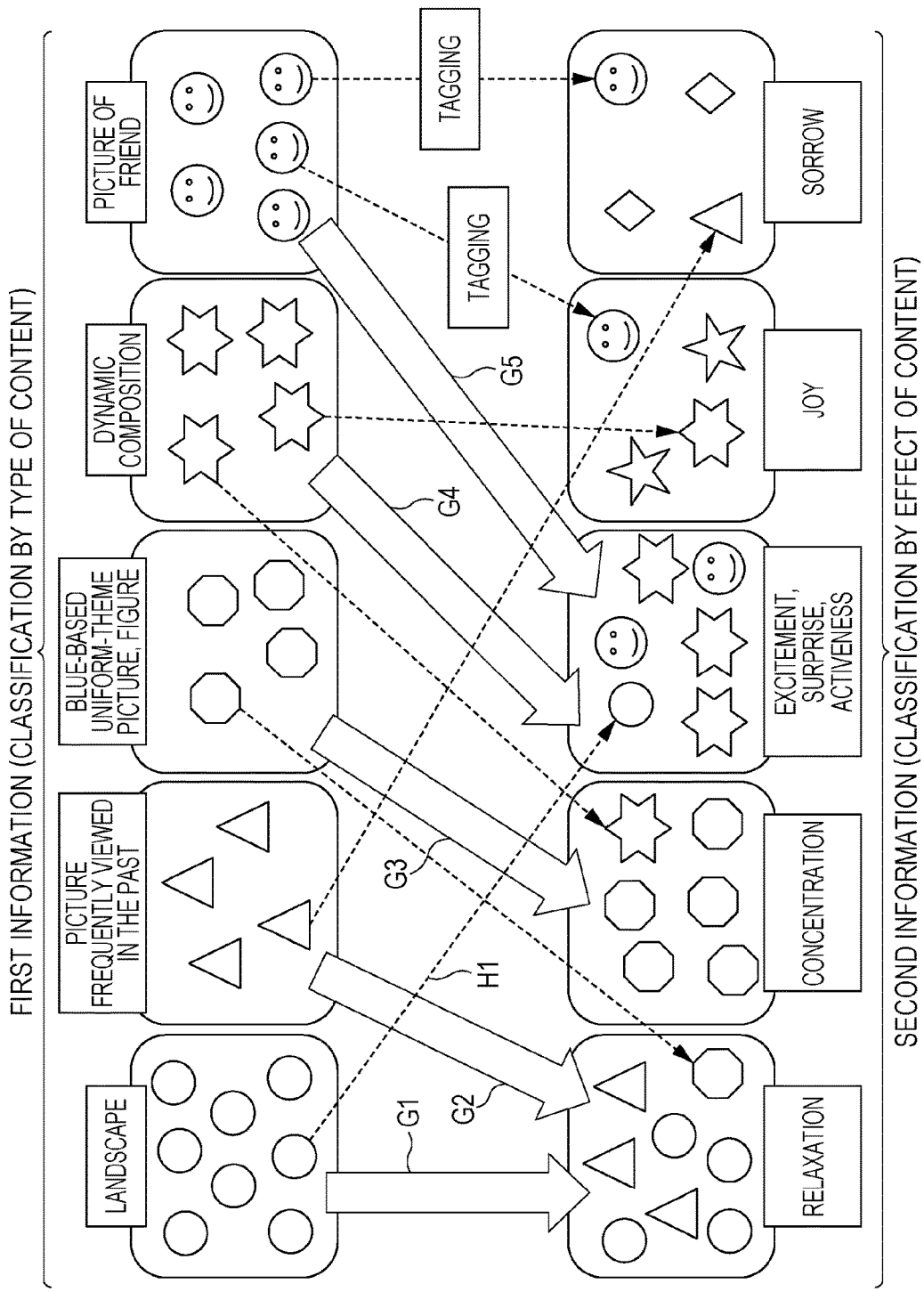
FIG. 6 illustrates examples of attribute information on stimulus presenting contents stored in a stimulus content database according to the first embodiment of the present disclosure.

FIG. 6 illustrates examples of attribute information on stimulus presenting contents. As shown in FIG. 6, the attribute information includes first information in which stimulus presenting contents are classified by the type of content, and second information in which stimulus presenting contents are classified by the effect to be applied to the mental state of a user.

As shown in FIG. 6, the first information is information in which stimulus presenting contents are classified by the type of content into "landscape," "picture frequently viewed in the past," "blue-based uniform-theme picture, figure," "dynamic composition," and "picture of friend." In the first information, by classifying stimulus presenting contents by the type of content, effects on the mental state of a user by similar contents can be expected. As shown in FIG. 6, for example, the contents in the first information classified into "landscape" and "picture frequently viewed in the past" can be expected to lead the mental state of the user mainly to "relaxation" as indicated by arrow G1 and arrow G2. Similarly, the contents in the first information classified into "blue-based uniform-theme picture, figure" can be expected to lead the mental state of the user mainly to "concentration" as indicated by arrow G3. Also, the contents in the first information classified into "dynamic composition" and "picture of friend" can be expected to lead the mental state of the user mainly to "excitement, surprise, activeness" as indicated by arrow G4 and arrow G5.

As shown in FIG. 6, the second information is information in which stimulus presenting contents are classified by the effects including "relaxation," "concentration," "excitement, surprise, activeness," "joy," and "sorrow." For example, in the second information, the contents classified into "landscape" in the first information may include stimulus presenting contents that attains an effect of "excitement, surprise, activeness" (see dotted arrow H1 from "landscape" in the first information to "excitement, surprise, activeness" in the second information in FIG. 6). Since such stimulus presenting contents can lead the mental state of the user to "relaxation" and "excitement, surprise, activeness," in the second information, the stimulus presenting contents of "landscape" into "relaxation" and "excitement, surprise, activeness." Also, in the second information, the stimulus presenting contents can be classified by the user intentionally applying tags to the effects of the stimulus presenting contents. For example, as shown in FIG. 6, if a picture that attains an effect of "joy" is included in "picture of friend," the user may apply a tag of "joy" to the picture, and may classify the picture into "joy." Similarly, if a picture that attains an effect of "sorrow" is included in "picture of friend," the user may apply a tag of "sorrow" to the picture, and may classify the picture into "sorrow." In the second information, by classifying the stimulus presenting contents by the effects of individual contents, the change amount of the mental state of the user by a stimulus presenting content can be further effectively expected.

Effect Difference Calculator

The effect difference calculator 19 calculates a difference between a first change amount of the mental state of a user by a stimulus presenting content and a second change amount of the mental state of the user expected on the basis of data in the user model database 17 and data in the stimulus content database 18. The first change amount is a change amount from the mental state of the user estimated before presentation of a stimulus presenting content, to the mental state of the user estimated after the presentation of the stimulus presenting content is started. The time point after the presentation of the stimulus presenting content is started is, for example, a time point immediately after the presentation of the stimulus presenting content is started, a time point during the presentation of the stimulus presenting content, or a time point in a period from when the presentation of the stimulus presenting content is ended to presentation of a next stimulus presenting content. The second change amount is an expected change amount expected on the basis of data in the user model database 17 and data in the stimulus content database 18 from the user mental state before the presentation of the stimulus presenting content to the user mental state after the presentation of the stimulus presenting content is started. If the difference between the first change amount and the second change amount is a predetermined value or larger in the effect difference calculator 19, the scenario creator 14 changes the scenario on the basis of the calculation result of the effect difference calculator 19. Also, the user model database 17 feeds back the calculation result of the effect difference calculator 19 and updates the user model. The stimulus content database 18 feeds back the calculation result of the effect difference calculator 19 and updates data on the expected change amount in the mental state of the user caused by the stimulus presenting content.

Operation

Next, an operation of the stimulus presenting system 10A (a stimulus presenting method) is described with reference to FIG. 7.

Figure 7:
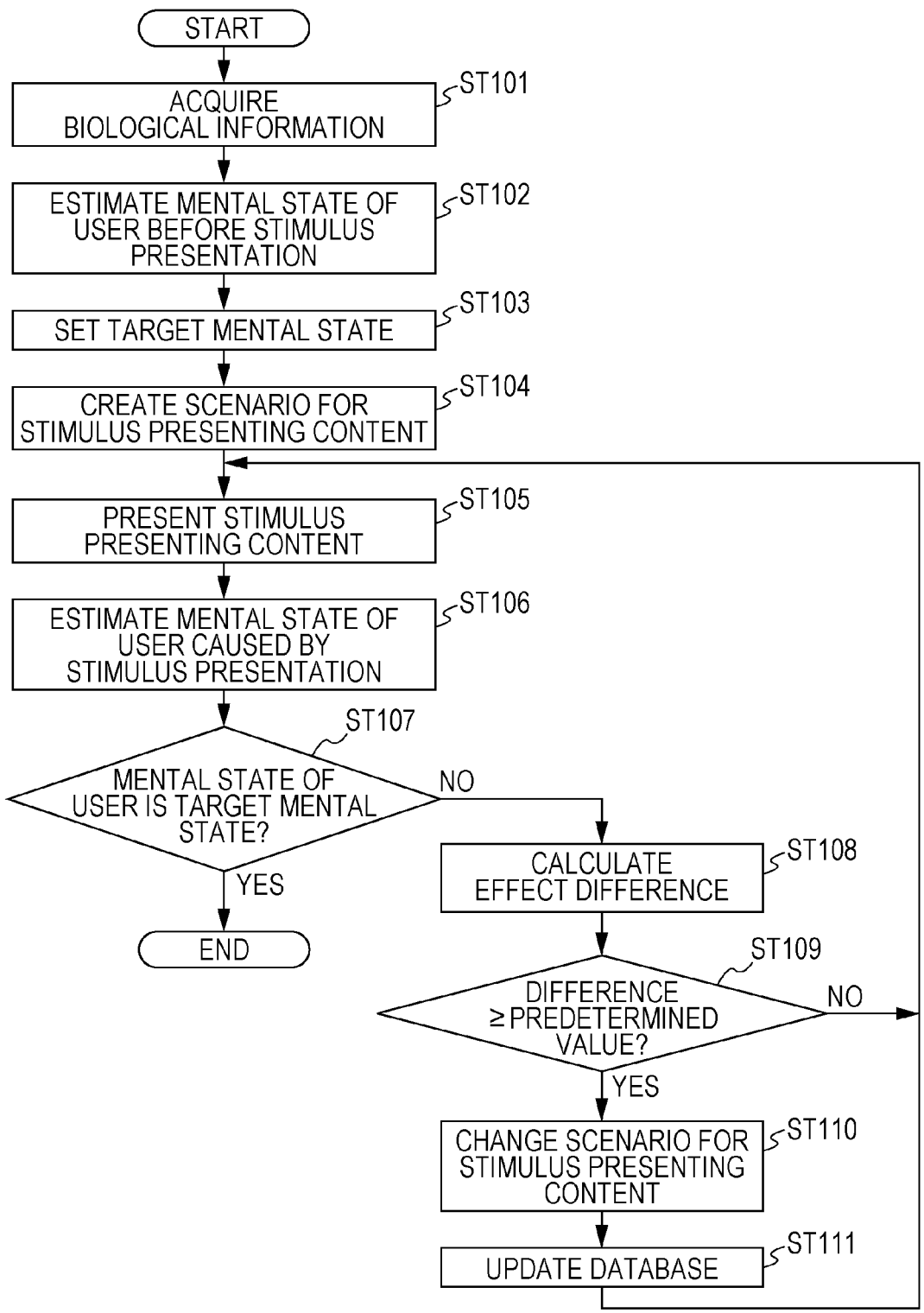
FIG. 7 is a flowchart of an operation of the stimulus presenting system according to the first embodiment of the present disclosure.

FIG. 7 is a flowchart for the operation of the stimulus presenting system 10A. Respective steps shown in FIG. 7 are executed by the computer 20. The steps shown in FIG. 7 are described in detail below.

As shown in FIG. 7, when the operation of the stimulus presenting system 10A is started, the flow goes to step ST101.

In step ST101, the biological information acquirer 11 (the pressure sensor 11a, the brain wave sensor 11b) acquires at least one piece of biological information on a user (a biological information acquiring step). In step ST101, the biological information acquirer 11 measures the heart rate, brain wave, and body motion of the user in real time as biological information.

In step ST102, the mental state estimator 12 estimates the mental state of the user before presentation of a stimulus (a mental state estimating step). In step ST102, the mental state estimator 12 estimates the mental state of the user on the basis of the biological information acquired in step ST101. The estimation for the mental state of the user uses the estimation examples shown in FIG. 3 as described above. Also, in step ST102, the mental state estimator 12 estimates the mental state of the user on the basis of a user model in the user model database 17.

In step ST103, the target state setter 13 sets a target mental state of the user (a target state setting step). In step ST103, the mental state of the user estimated in step ST102 is displayed on the display section of the target state setter 13. The user inputs a target mental state from the input operation section on the basis of the mental state of the user displayed on the display section. For example, the target state setter 13 sets the target mental state on the basis of the information input from the input operation section.

In step ST104, the scenario creator 14 creates a scenario for a stimulus presenting content to be presented to the user (a scenario creating step). In step ST104, the scenario creator 14 creates a scenario (the order of presentation, the period of presentation, and the number of times of presentation) for at least one stimulus presenting content including at least one of video and sound on the basis of the target mental state set in step ST103. The scenario is created on the basis of the user model in the user model database 17 and the data in the stimulus content database 18 so as to include a stimulus presenting content with a higher effect to lead the mental state of the user to the target mental state. Data on the scenario created by the scenario creator 14 is transmitted to the content presenter 15.

In step ST105, the content presenter 15 presents the stimulus presenting content to the user (a content presenting step). In step ST105, the content presenter 15 presents the stimulus presenting content to the user on the basis of the scenario created in step ST104.

In step ST106 and step ST107, the mental state estimator 12 estimates the mental state of the user changed as the result of the presentation of the stimulus presenting content, and the mental state determiner 16 determines whether or not the mental state after the change attains the target mental state (a mental state determining step). In step ST106, the mental state of the user during the presentation of the stimulus presenting content or after the presentation of the stimulus presenting content is estimated. To be specific, the biological information acquirer 11 acquires the biological information on the user during the presentation of the stimulus presenting content or after the presentation of the stimulus presenting content, and the mental state estimator 12 estimates the mental state of the user on the basis of the biological information acquired by the mental state estimator 12. That is, in step ST106, the biological information acquirer 11 acquires biological information on the user after presentation of at least one stimulus presenting content is started on the basis of the scenario, and the mental state estimator 12 estimates the mental state of the user on the basis of the acquired biological information.

In step ST107, the mental state determiner 16 determines whether or not the mental state (a second mental state) of the user estimated in step ST106 attains the target mental state set in step ST103. In step ST107, if the mental state determiner 16 determines that the mental state of the user attains the target mental state (YES), the content presenter 15 ends the presentation of the stimulus presenting content. In contrast, in step ST107, if the mental state determiner 16 determines that the mental state of the user does not attain the target mental state (NO), the flow goes to step ST108.

In step ST108, a difference between a first change amount of the mental state of the user caused by the presentation of the stimulus presenting content and a second change amount of the mental state of the user caused by the presentation of the stimulus presenting content and expected on the basis of the data in the user model database 17 and the data in the stimulus content database 18 is calculated (an effect difference calculating step). In step ST108, in case of an initial operation, the effect difference calculator 19 calculates the first change amount from the mental state (the first mental state) of the user before the presentation of the stimulus estimated in step ST102 to the mental state (the second mental state) of the user during the presentation or after the presentation of the stimulus estimated in step ST106. Also, the effect difference calculator 19 calculates the second change amount (an expected change amount) of the mental state of the user expected after the presentation of the stimulus presenting content, on the basis of the data in the user model database 17 and the data in the stimulus content database 18.

In step ST108, if the stimulus presenting system 10A repeats the operation from step ST105 to step ST111, the first change amount is a change amount from the mental state estimated in step ST106 in the previous operation to the mental state estimated in step ST106 in the current operation as the result of the presentation of the stimulus presenting content in step ST105 in the current operation. Similarly, the second change amount is also a change amount from the mental state estimated in step ST106 in the previous operation to the mental state of the user expected on the basis of the data in the user model database 17 and the data in the stimulus content database 18.

In step ST109, it is determined whether or not the difference calculated in step ST108 is a predetermined value or larger. If it is determined that the difference calculated by the effect difference calculator 19 is the predetermined value or larger (YES) in step ST109, it is determined that the effect of the presented stimulus presenting content is lower than expected, or it is determined that the effect is higher than expected. Then, the flow goes to step ST110. In contrast, if it is determined that the difference calculated by the effect difference calculator 19 is not the predetermined value or larger (NO) in step ST109, it is determined that the effect of the presented stimulus presenting content is within an expected range, and the flow returns to step ST105.

In step ST110, the scenario creator 14 changes the scenario for the stimulus presenting content (a scenario changing step). To be specific, in step ST110, the scenario creator 14 changes, for example, the period of presentation, the number of times of presentation, etc., of a stimulus presenting content to be presented after a stimulus presenting content being a subject of determination. At this time, the scenario creator 14 may change the stimulus presenting content to be presented later. In step ST110, if it is determined that the presented stimulus presenting content has a lower effect on the mental state of the user than expected, the scenario creator 14 changes the scenario to decrease the period of presentation, the number of times of presentation, etc., of a stimulus presenting content which is similar to the stimulus presenting content determined to have the lower effect, from among stimulus presenting contents to be presented after the stimulus presenting content being the subject of determination. Alternatively, the scenario creator 14 may change a stimulus presenting content which is similar to the stimulus presenting content determined to have a lower effect from among stimulus presenting contents to be presented after the stimulus presenting content being the subject of determination, into another stimulus presenting content.

At this time, the scenario creator 14 determines that the effect of leading the mental state to the target mental state is low for contents in the same classification, according to classification of contents into types on the basis of the first information of the attribute information in the stimulus content database 18. In contrast, if it is determined that the presented stimulus presenting content has a higher effect on the mental state of the user that expected, the scenario creator 14 changes the scenario to increase the period of presentation, the number of times of presentation, etc., of a stimulus presenting content which is similar to the stimulus presenting content determined to have a higher effect. The scenario creator 14 may add a stimulus presenting content which is similar to the content determined to have the higher effect from among stimulus presenting contents to be presented after the stimulus presenting content being the subject of determination. At this time, the scenario creator 14 determines that the effect of leading the mental state to the target mental state is high for contents in the same classification, according to classification of contents into types on the basis of the first information of the attribute information in the stimulus content database 18. Also, the scenario is changed on the basis of the user model database 17 and the stimulus content database 18.

In step ST111, the data stored in the database (the user model database 17 and the stimulus content database 18) is updated (a database updating step). In step ST111, the user model database 17 corrects the user model of the user upon determination that the attribution of the presented stimulus presenting content has a lower or higher effect of leading the mental state of the user to the target mental state. Also, the stimulus content database 18 corrects the data on expected change amount of the mental state to be applied by the stimulus presenting content to the user on the basis of the presented stimulus presenting content. When the step ST111 is ended, the flow returns to step ST105.

Advantageous Effects

With the stimulus presenting system 10A according to the first embodiment, the following advantageous effects can be attained.

The stimulus presenting system 10A according to the first embodiment estimates the mental state before the presentation of the stimulus presenting content on the basis of the biological information on the user, and then sets the target mental state of the user. Also, the stimulus presenting system 10A estimates the mental state during the presentation of the stimulus presenting content or after the presentation of the stimulus presenting content, and determines whether or not the mental state of the user changed by the stimulus presenting content attains the target mental state. With this configuration, the stimulus presenting system 10A can efficiently select and present a content on the basis of a change in mental state of the user. Accordingly, the mental state of the user can be efficiently led to the target mental state.

In the stimulus presenting system 10A, the scenario creator 14 creates the scenario for the stimulus presenting content on the basis of the user model in the user model database 17 and the data in the stimulus content database 18. Accordingly, the scenario creator 14 can customize the scenario for each user, and create the scenario to include the stimulus presenting content being highly effective on the mental state of the user. Accordingly, the stimulus presenting system 10A can efficiently lead the mental state of the user to the target mental state.

With the stimulus presenting system 10A, the effect difference calculator 19 calculates the difference between the actual change in mental state of the user caused by the presentation of the stimulus presenting content and the expected change amount expected on the basis of the user model database 17 and the stimulus content database 18. The stimulus presenting system 10A checks the effect of the presented stimulus presenting content with reference to the calculated difference, and changes the scenario by the scenario creator 14 if it is determined that the effect is lower or higher than expected. With this configuration, the stimulus presenting system 10A can change the scenario so as to include a stimulus presenting content a the higher effect of leading the mental state of the user to the target mental state during the presentation of the stimulus presenting content. Also, the stimulus presenting system 10A corrects the user model in the user model database 17 and the data in the stimulus content database 18 on the basis of the difference in effect. With this configuration, the stimulus presenting system 10A feeds back the data on the effect of the presented stimulus presenting content successively, and can present the optimal stimulus presenting content depending on the tendency of the user or the mental state of the user at that time in real time. As the result, the stimulus presenting system 10A can efficiently lead the mental state of the user to the target mental state.

In the first embodiment, the example has been described in which the biological information acquirer 11 is the pressure sensor that acquires the heart rate and body motion of the user, and the brain wave sensor that acquires the brain wave of the user. However, the biological information acquirer 11 is not limited thereto. The biological information acquired by the biological information acquirer 11 may be any information as long as the information allows the mental state of the user to be estimated. For example, biological information acquirer 11 may use a non-restraint non-invasive sensor, such as an image sensor that acquires the facial expression or body motion of the user, a vibration sensor that acquires a vibration, or a sound sensor that acquires a sound, may be used. By using such a sensor, the biological information on the user can be more correctly acquired.

Also, the example has been described in which the biological information acquirer 11 acquires the biological information in real time; however, it is not limited thereto. For example, the biological information may be acquired when the mental state estimator 12 estimates the mental state of the user. With this configuration, the load on the system can be decreased.

In the first embodiment, the mental state of the user is defined and described as relaxation, concentration, excitement, surprise, joy, and sorrow. However, the mental state of the user is not limited thereto. For example, the definition of the mental state may include anger and pleasure.

In the first embodiment, the mental state estimator 12 may estimate the mental state of the user on the basis of an average value of plural pieces of biological information acquired in a predetermined period (for example, an average value or the like when the heart rate per minute is acquired five times). With this configuration, the mental state estimator 12 can correctly estimates the mental state of the user.

In the first embodiment, the example has been described in which the user manually sets the target mental state by using the input operation section of the target state setter 13; however, it is not limited thereto. For example, the target state setter 13 may automatically set the target mental state with the computer 20. Alternatively, the target state setter 13 may store a target mental state set in the past in association with a set time as history information in a readable and writable storage medium, such as a memory or a hard disk. For example, the target state setter 13 may read the history information about the target mental state from the storage medium, and set a target mental state on the basis of the read history information. For example, a target mental state associated with a time being the closest to the current time among the history information on the target mental state may be set as a target mental state to be set this time. Alternatively, the target state setter 13 may check the contents of the target mental state set in the past and included in the history information, and set target mental states which have the same contents and set a predetermined number of times or more, as a target mental state which is to be set this time. For example, if the number of target mental states corresponding to relaxation is larger than a predetermined number among target mental states set in the past and included in the history information, the target state setter 13 sets relaxation as a target mental state which is to be set this time.

Alternatively, for example, if the number of target mental states corresponding to relaxation is smaller than a predetermined number among target mental states set in the past and included in the history information, the target state setter 13 may set relaxation as a target mental state which is to be set this time.

With this configuration, the stimulus presenting system 10A can omit an input operation by the user, and usability can be improved.

In the first embodiment, the example has been described in which the stimulus presenting content includes at least one content including video or sound; however, it is not limited thereto. For example, the stimulus presenting content may be a content including a stimulus, such as a vibration, an odor, light, wind, a change in temperature, etc. Since these various stimuli are included, the mental state of the user can be efficiently led to the target mental state.

In the first embodiment, the scenario created by the scenario creator 14 has been described by using the scenarios A to E shown in FIG. 4; however, the scenario is not limited to these scenarios. For example, the scenario may be created with various types of contents, such as a travel, a portrait, a vehicle, and a simple figure. Also, in the first embodiment, the scenario A including the 30 contents has been described as the example with reference to FIG. 5. However, it is not limited thereto. The scenario may be created by using a desirable number of contents. Further, when it is judged that the heart rate is stable, in processing of searching a content having a close attribution, processing of expanding the search range and treating a content having a slightly far attribution may be added. Accordingly, in the stable heart rate state, by presenting contents according to the scenario with a slightly high randomness, a stimulus can be mentally effectively transmitted.

In the first embodiment, the example has been described in which the scenario creator 14 creates the scenario for the stimulus presenting content on the basis of the data in the user model database 17 and the data in the stimulus content database 18. However, it is not limited thereto. For example, the scenario creator 14 may create a scenario for a stimulus presenting content on the basis of at least one of the data in the user model database 17 and the data in the stimulus content database 18.

In the first embodiment, the example has been described in which the attribute information on the stimulus presenting contents held by the stimulus content database 18 is classified by the type of content and the effect applied to the mental state of the user; however, it is not limited thereto. For example, the attribute information may be classified by at least one of the type of content and the effect applied to the mental state of the user. The tendency of the user may be acquired from the number of contents for each piece of attribution information in the stimulus content database 18, and the effectiveness of the user model database 17 may be corrected. To be specific, correction may be provided so that the effectiveness of the contents is high if there are many contents relating to joy.

In the first embodiment, at least one of the mental state estimator 12, the scenario creator 14, and the mental state determiner may include a processor. At least one of the mental state estimation (S102), the scenario creation (S104), and the mental state determination (106) may be executed by a processor.

Second Embodiment

General Configuration

A stimulus presenting system according to a second embodiment of the present disclosure is described with reference to FIG. 8.

Figure 8:
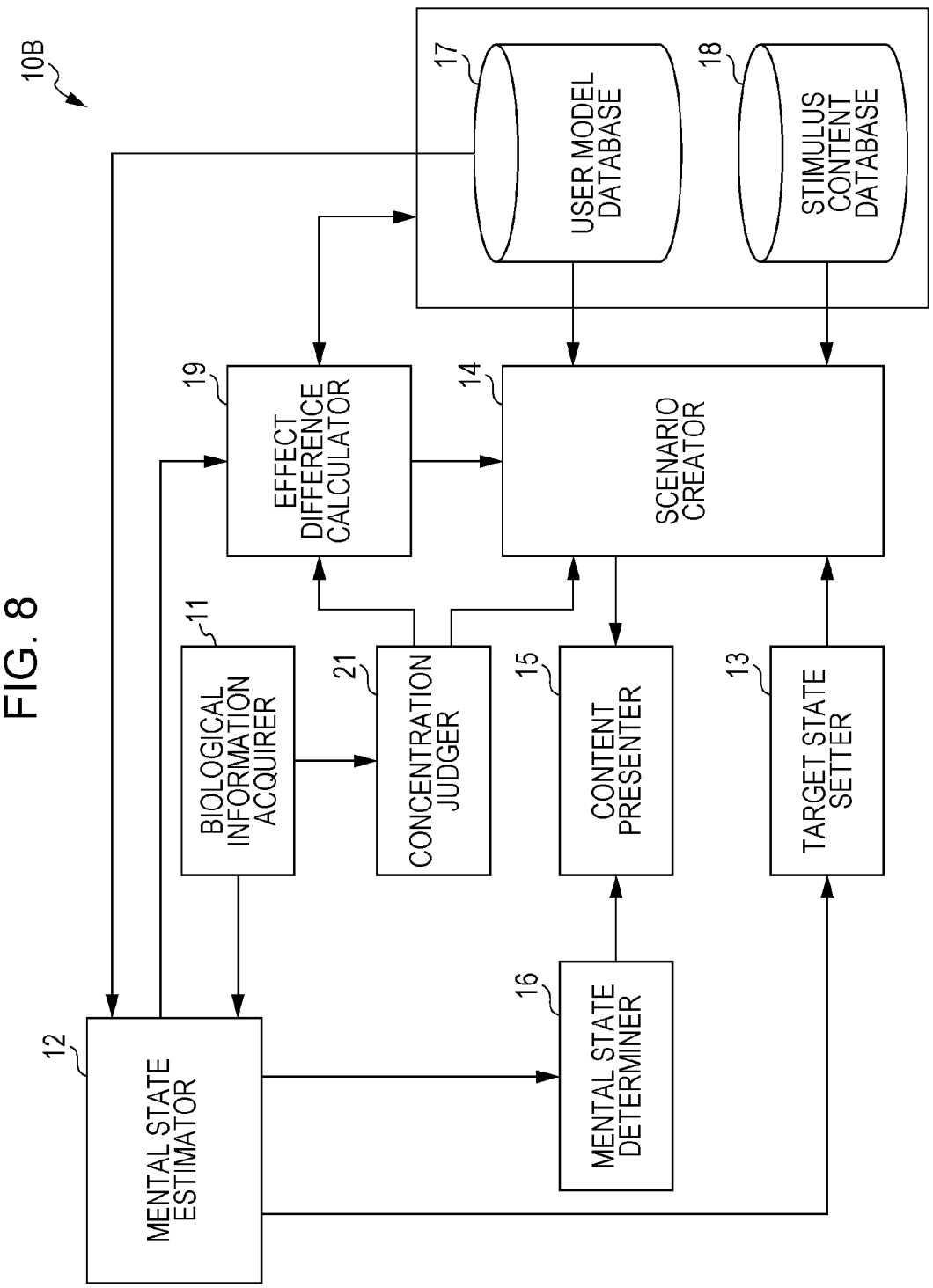
FIG. 8 is a block diagram of a configuration of a stimulus presenting system according to a second embodiment of the present disclosure.

FIG. 8 is a block diagram of a configuration of the stimulus presenting system according to the second embodiment. In the second embodiment, points different from the first embodiment are mainly described. In the second embodiment, the configurations the same as or equivalent to those of the first embodiment are described while the same reference signs are applied to these configurations. Also, in the second embodiment, the redundant description overlapping the first embodiment is omitted.

As shown in FIG. 8, a stimulus presenting system 10B includes a biological information acquirer 11, a mental state estimator 12, a target state setter 13, a scenario creator 14, a content presenter 15, a mental state determiner 16, a user model database 17, a stimulus content database 18, an effect difference calculator 19, and a concentration judger 21. Also, the stimulus presenting system 10B is configured with a computer mounted thereon. These components are controlled by the computer 20.

The computer of the stimulus presenting system 10B includes, for example, a processing circuit (not shown) such as a central processing unit (CPU), and a first storage medium, similarly to the computer of the stimulus presenting system 10A described in the first embodiment.

The first storage medium stores, for example, respective programs that cause the computer to function as the mental state estimator 12, the scenario creator 14, the mental state determiner 16, the effect difference calculator 19, and the concentration judger 21.

Also, the first storage medium stores, for example, respective programs that control the biological information acquirer 11, the target state setter 13, and the content presenter 15.

Also, the first storage medium stores programs that make accesses (reading, writing, etc.) to the user model database 17 and the stimulus content database 18.

When the processing circuit of the computer executes these programs stored in the first storage medium, the computer causes the mental state estimator 12, the scenario creator 14, the mental state determiner 16, the effect difference calculator 19, and the concentration judger 21 to function, controls the biological information acquirer 11, the target state setter 13, and the content presenter 15, and makes accesses to the user model database 17 and the stimulus content database 18.

Alternatively, the computer of the stimulus presenting system 10B may be provided by using an integrated circuit incorporating the functions and operations to be provided by executing the programs stored in the above-described first storage medium with the processing circuit.

The stimulus presenting system 10B according to the second embodiment differs from the stimulus presenting system 10A according to the first embodiment in that the stimulus presenting system 10B includes the concentration judger 21.

In the second embodiment, the reason why the concentration judger 21 is provided is described.

For example, if a user does not watch (does not concentrate on) a stimulus presenting content, the stimulus presenting content does not give an influence on the mental state of the user. At this time, in the effect difference calculator 19, the difference between the change amount of the mental state of the user and the expected change amount based on the database becomes a predetermined value or larger, and the scenario is changed and the database is updated. However, in this case, even if the scenario is changed and the database is updated on the basis of the calculated difference, since the user does not concentrate on the stimulus presenting content, the mental state of the user cannot be led to the target mental state. Therefore, the stimulus presenting system 10B includes the concentration judger 21 to judge whether the user concentrate on the stimulus presenting content or not, and correct the difference calculated by the effect difference calculator 19 in accordance with the judgment result.

Next, the concentration judger 21 is described in detail.

Concentration Judger

As shown in FIG. 8, the concentration judger 21 is connected to the biological information acquirer 11, the effect difference calculator 19, and the scenario creator 14. The concentration judger 21 judges whether or not the user concentrates on the stimulus presenting content presented by the content presenter 15. To be specific, when a concentration judging content different from the stimulus presenting content is presented, the concentration judger 21 judges whether or not the user concentrates on the stimulus presenting content on the basis of an event related potential (ERP) corresponding to brain wave information being an example of brain activity information included in biological information acquired by the biological information acquirer 11.

The concentration judging content is described.

The concentration judging content is a content less relating to (markedly different from) the stimulus presenting content included in the scenario created by the scenario creator 14. The concentration judging content according to the second embodiment includes a content of attribute information different from the attribute information on the stimulus presenting content held in the stimulus content database 18. For example, If a stimulus presenting content including a "joyful scene" belonging to the effect of "joy" as attribute information is presented, a concentration judging content including a "sorrowful scene" belonging to the effect of "sorrow" as attribute information is presented. Also, a content is selected so that the user can clearly feel a change in composition, for example, by mixing a content with a simple composition into a picture containing many objects in view of composition.

Figure 9:
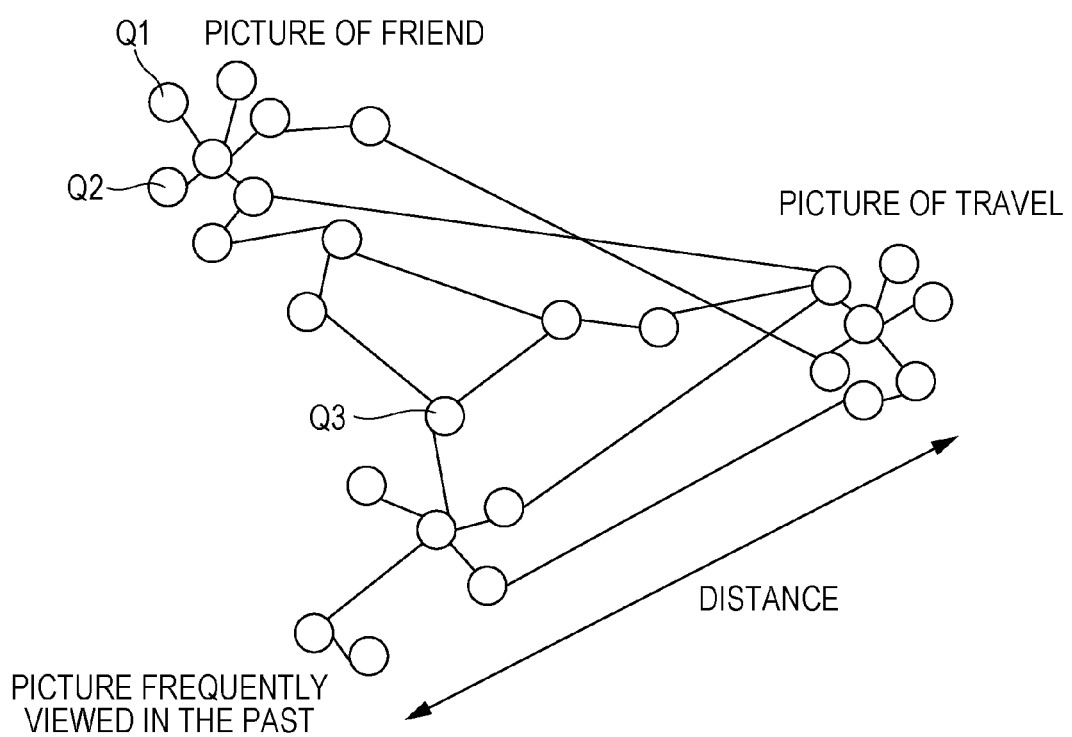
FIG. 9 is a network diagram expressing a similarity among a plurality of picture contents.

FIG. 9 is a network diagram expressing a similarity among a plurality of picture contents by at least one characteristic owned by a picture content. As shown in FIG. 9, pictures of friends, pictures frequently viewed in the past, and pictures of travel are arranged on a network. Pictures of friends in a group are arranged close to each other in view of visualized distance on the network. For example, as shown in FIG. 9, a picture Q1 of friend and another picture Q2 of friend are arranged close to each other. Also, if there is a picture of friend frequently viewed in the past, the picture is arranged close to each of respective groups of pictures. For example, as shown in FIG. 9, a picture Q3 of friend frequently viewed in the past is arranged close to both the group of pictures of friends and the group of pictures frequently viewed in the past. Such a picture at a large distance in the arrangement on the network diagram is highly possibly recognized as a different type of picture by the user. In this way, by using the network diagram as shown in FIG. 9, a picture at a large distance may be used as a low-frequency image for concentration judgment.

When the concentration judger 21 executes concentration judgment, the scenario creator 14 creates a scenario for concentration judgment including a stimulus presenting content and a concentration judging content. Also, the scenario for concentration judgment is created so that the concentration judging content is presented with a lower frequency than the frequency of the stimulus presenting content.

The scenario for concentration judgment is described with reference to FIG. 10.

Figure 10:
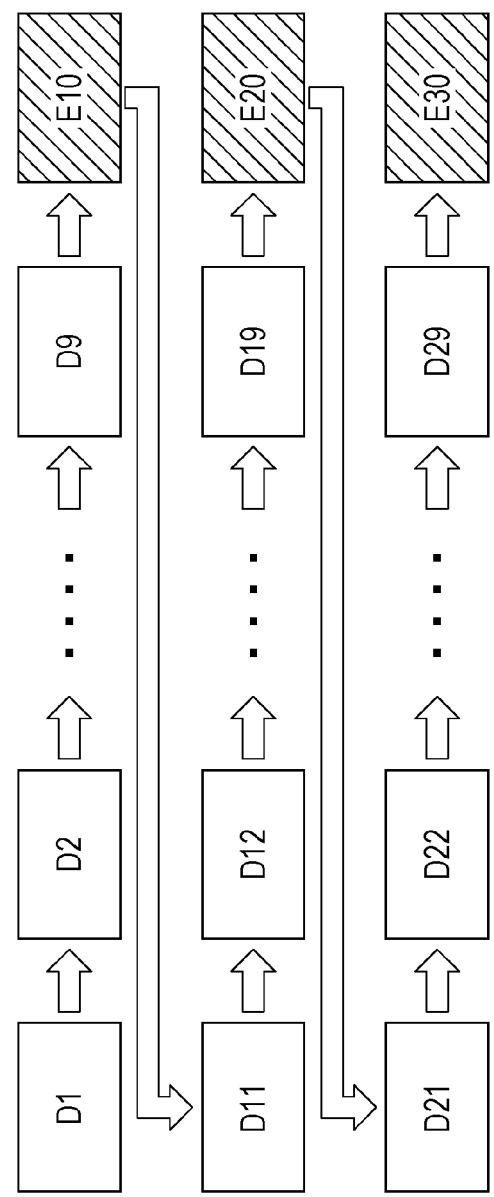
FIG. 10 illustrates an example of a scenario for concentration judgment created by a scenario creator according to the second embodiment of the present disclosure.

FIG. 10 is an example of a scenario for concentration judgment created by the scenario creator 14. As shown in FIG. 10, the scenario for concentration judgment is created to present stimulus presenting contents D1 to D9, D11 to D19, and D21 to D29, and concentration judging contents E10, E20, and E30. The stimulus presenting contents D1 to D9, D11 to D19, and D21 to D29 are, for example, contents having attribute information being "joy" (contents based on the scenario D in FIG. 4). The concentration judging contents E10, E20, and E30 are contents having attribute information being "sorrow" (contents based on the scenario E in FIG. 4) different from the attribute information ("joy") of the stimulus presenting contents. In the scenario for concentration judgment, a concentration judging content is presented once every time when a stimulus presenting content is presented a predetermined number of times. For example, as shown in FIG. 10, when the stimulus presenting contents D1 to D9 are presented, the concentration judging content E10 is presented. After the concentration judging content E10 is presented, the contents are presented in the order of the stimulus presenting contents D11 to D19, the concentration judging content E20, the stimulus presenting contents D21 to D29, and the concentration judging content E30. In this way, the scenario for concentration judgment is created to present the stimulus presenting contents with a higher frequency than the frequency of the concentration judging contents and to present the concentration judging contents with a lower frequency than the frequency of the stimulus presenting contents (for example, presentation is provided with the ratio of the stimulus presenting contents to the concentration judging contents of 9:1).

Also, the scenario creator 14 selects a concentration judging content used for a scenario for concentration judgment, from contents in the stimulus content database. The scenario creator 14 checks attribute information on a content immediately before presentation of a concentration judging content. For example, the attribute information on the stimulus presenting contents D9, D19, and D29 used for the scenario for concentration judgment are checked, and contents with low similarities are selected as concentration judging contents from the stimulus content database. For example, the stimulus presenting content D9 is described. The scenario creator 14 may check attribute information on the stimulus presenting content D9, and select a content having attribute information with the lowest similarity to the attribute information on the stimulus presenting content D9, as the concentration judging content E10 from the stimulus content database.

Alternatively, if the stimulus presenting content D9 has plural pieces of attribute information, the scenario creator 14 may select a content with the smallest number of pieces of attribute information having common contents, as the concentration judging content E10 from the stimulus content database.

Also, the scenario creator 14 may select a content at a predetermined distance or larger from the stimulus presenting content D9, as the concentration judging content E10 from the stimulus content database by using the network diagram as shown in FIG. 9.

Next, a method of executing concentration judgment by measuring an event related potential (ERP) is described.

An event related potential is a potential that is generated in relation to a certain event. The event related potential can be measured by the biological information acquirer 11 (for example, the brain wave sensor 11b) measuring brain wave information. The concentration judger 21 executes concentration judgment of the user by measuring a P300 waveform in the event related potential.

The P300 waveform is described.

The P300 waveform is one of brain wave reactions. If different high-frequency and low-frequency stimuli are applied to the user, the P300 waveform is a waveform (a brain waveform) having a positive amplitude peak generated when about 300 ms has elapsed since a low-frequency stimulus is applied. For example, if images of mountains are provided to the user nine times and an image of a person is provided to the user once, the user recognizes that the image of the person is different from the images of the mountains. A change generated in brain wave at this time appears in the measurement result of the event related potential as the P300 waveform.

Figure 11:
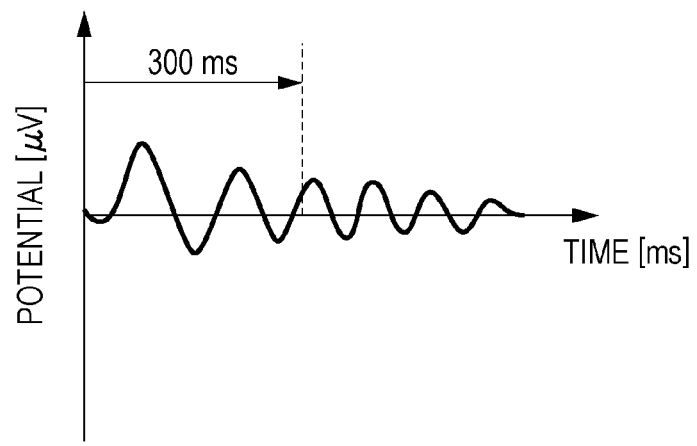
FIG. 11 illustrates a measurement result of brain wave information when a high-frequency stimulus is given to a user.
Figure 12:
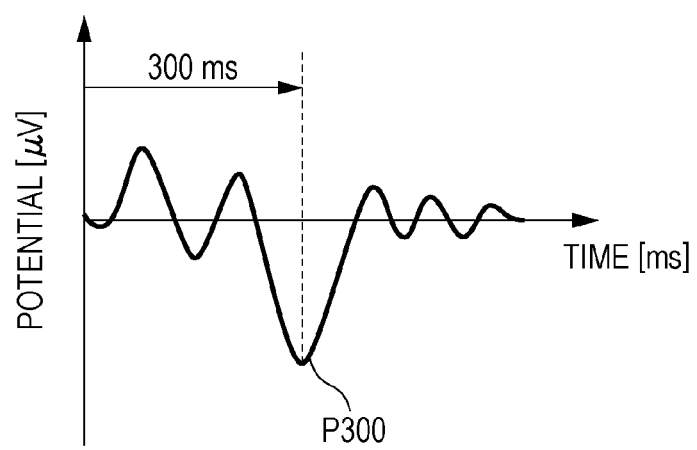
FIG. 12 illustrates a measurement result of brain wave information when a low-frequency stimulus is given to a user.

FIG. 11 illustrates a measurement result of brain wave information when a high-frequency stimulus is given to a user. FIG. 12 illustrates a measurement result of brain wave information when a low-frequency stimulus is given to a user. As shown in FIG. 11, when the high-frequency stimulus is presented to the user, a large change in potential is not found near a position at 300 ms from the stimulus presentation. In contrast, as shown in FIG. 12, when the low-frequency stimulus is presented to the user, the P300 waveform having a large amplitude is generated near a position at 300 ms from the stimulus presentation. FIGS. 11 and 12 are images of brain waveforms for easier understanding of the description.

The P300 waveform can be obtained by calculating the difference between a potential immediately after a high-frequency stimulus (a stimulus presenting content) is applied and a potential (an event related potential) immediately after a low-frequency stimulus (a concentration judging content) is applied. Alternatively, the P300 waveform may be measured by using a sum average of event related potentials measured a plural number of times.

As described above, the concentration judger 21 can judge whether or not the user concentrates by measuring the P300 waveform when the concentration judging content is presented. If the concentration judger 21 judges that the user does not concentrate, the result of difference calculated by the effect difference calculator 19 is corrected. To be specific, the concentration judger 21 corrects the result of difference to 0. Also, if the concentration judger 21 judges that the user does not concentrate, a sound is generated from the loudspeaker of the content presenter 15 so that the user concentrates on the stimulus presenting content.

In FIGS. 11 and 12, the measurement result of the brain wave information is illustrated as an example of the measurement result of the brain activity information when a high-frequency stimulus and a low-frequency stimulus are applied to the user. Similar results can be obtained even for the measurement result of brain magnetic field information. The brain wave sensor 11b detects a change in electric signal (current) flowing through the brain in accordance with the activity state of the brain, as a change in potential.

If the electric signal (current) flowing through the brain changes in accordance with the activity state of the brain, the magnetic field changes in accordance with the change. Accordingly, even with the configuration in which the biological information acquirer 11 includes a magnetic sensor and brain magnetic field information is acquired from information (magnetic field) detected by the magnetic sensor, a change corresponding to the above-described waveform can be measured on the basis of the measurement result of the brain magnetic field information.

Hence, the concentration judger 21 may judge whether or not the user concentrates by calculating the difference between a magnetic field immediately after a high-frequency stimulus (a stimulus presenting content) is applied and a magnetic field immediately after a low-frequency stimulus (a concentration judging content) is applied.

That is, the concentration judger 21 may compare first brain activity information included in biological information acquired in a period after the presentation of the concentration judging content and before presentation of a next content with second brain activity information included in biological information acquired during presentation of a stimulus presenting content other than the concentration judging content, judge that the user concentrates if a difference between the first brain activity information and the second brain activity information is a predetermined amount or more, and judge that the user does not concentrate otherwise.

Operation

Next, an operation (a stimulus presenting method) of the stimulus presenting system 10B is described with reference to FIG. 13.

Figure 13:
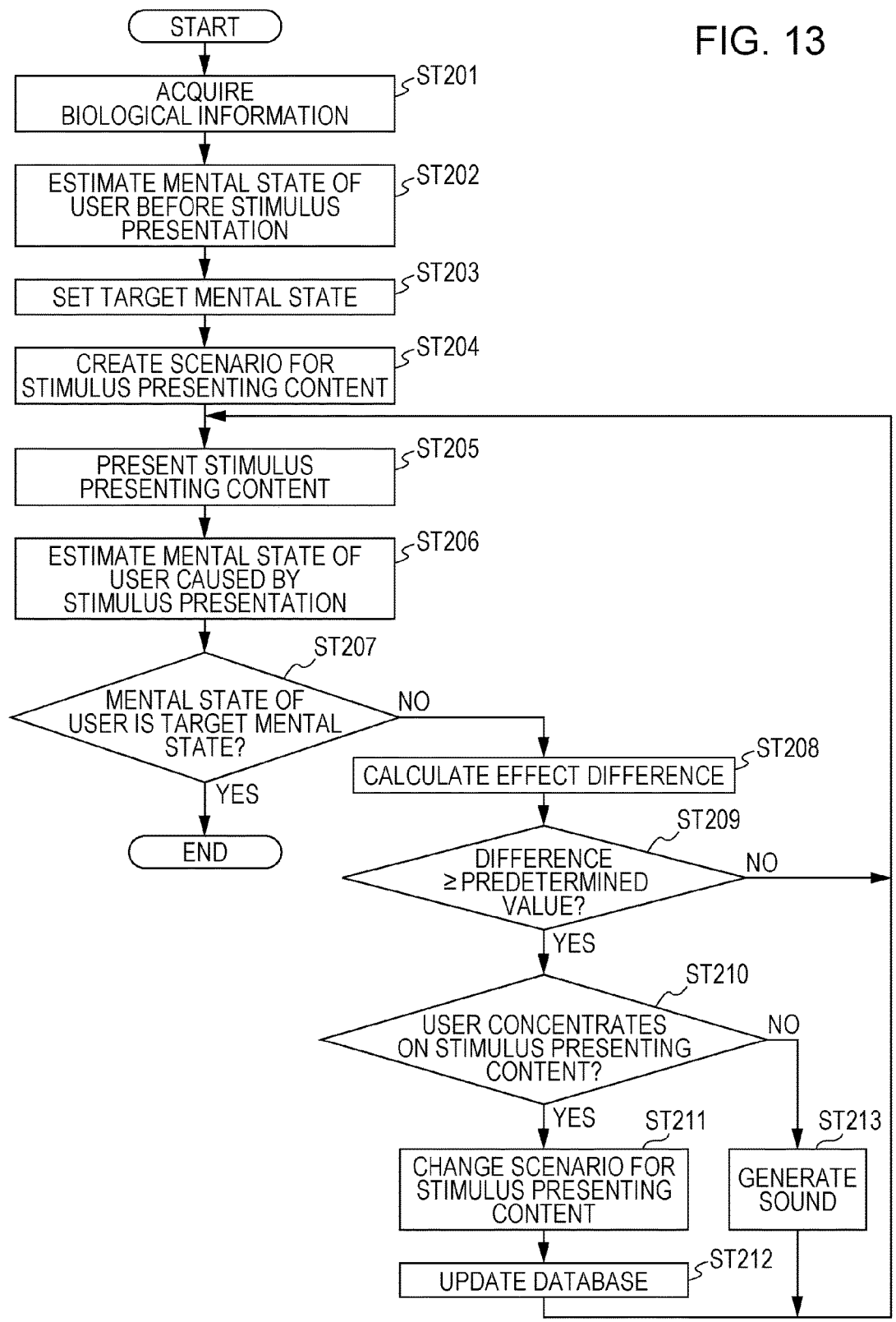
FIG. 13 is a flowchart of an operation of the stimulus presenting system according to the second embodiment of the present disclosure.

FIG. 13 is a flowchart for the operation of the stimulus presenting system 10B. Respective steps shown in FIG. 13 are executed by the computer 20. The steps shown in FIG. 13 are described in detail below. Steps ST201 to ST209 of the stimulus presenting system 10B are operations similar to those of steps ST101 to ST109 (see FIG. 7) of the stimulus presenting system 10A, and hence the description is omitted.

In step ST210, if the difference calculated by the effect difference calculator 19 in step ST209 is a predetermined value or larger, it is determined whether or not the user concentrates on the stimulus presenting content (a concentration judging step). In step ST210, the scenario creator 14 creates a scenario for concentration judgment to present a stimulus presenting content with high frequency and present a concentration judging content with low frequency. Then, the content presenter 15 presents the stimulus presenting content and the concentration judging content on the basis of the scenario for concentration judgment. The concentration judger 21 judges whether the P300 waveform is generated or not by measuring the brain wave information (the event related potential) in a period after the content presenter 15 presents the concentration judging content and before a next content is presented.

The time point after the concentration judging content is presented is, for example, a time point immediately after the presentation of the concentration judging content is started, or a time point after the presentation of the concentration judging content is ended.

The next content after the concentration judging content is presented is a stimulus presenting content in the example shown in FIG. 10.

In step ST210, if the concentration judger 21 judges that the user concentrates on the stimulus presenting content (the P300 waveform is generated), the flow goes to step ST211. In contrast, if the concentration judger 21 judges that the user does not concentrate on the stimulus presenting content (the P300 waveform is not generated), the flow goes to step ST213.

In step ST211, the scenario creator 14 changes the scenario for the stimulus presenting content (a scenario changing step). In step ST211, the scenario creator 14 creates a scenario including a stimulus presenting content that highly effectively leads the mental state of the user to the target mental state, similarly to step ST110 in FIG. 7.

In step ST212, the data stored in the database (the user model database 17 and the stimulus content database 18) is updated (a database updating step). In step ST212, the data in the database is updated on the basis of the calculation result of the effect difference calculator 19 similarly to step ST111 shown in FIG. 7. When the step ST212 is ended, the flow returns to step ST205.

In step ST213, a sound is generated from the content presenter 15 so that the user concentrates on the stimulus presenting content (a sound generating step). In step ST213, a sound (for example, a beep sound) for drawing attention is reproduced from the loudspeaker of the content presenter 15. Then, the content presenter 15 returns the setting from the scenario for concentration judgment to the original scenario. When the step ST213 is ended, the flow returns to step ST205.

Advantageous Effects

With the stimulus presenting system 10B according to the second embodiment, the following advantageous effects can be attained.

The stimulus presenting system 10B according to the second embodiment judges whether or not the user concentrates on the stimulus presenting content by measuring the event related potential when the concentration judging content is presented if the effect of the stimulus presenting content is markedly different from the expected effect. With this configuration, the data relating to the effect of the stimulus presenting content when the user does not concentrate can be eliminated, and hence the mental state of the user can be further efficiently led to the target state.

In the second embodiment, the example has been described in which the concentration judger 21 executes concentration judgment if the difference calculated by the effect difference calculator 19 is a predetermined value or larger; however, it is not limited thereto. The concentration judger 21 may determine whether or not concentration judgment is executed on the basis of the calculation results of differences obtained by a plural number of times of calculation. For example, the concentration judger 21 may execute concentration judgment if the difference in effect calculated by the effect difference calculator 19 is continuously a predetermined value or larger. Alternatively, the concentration judger 21 may execute concentration judgment if an average value of differences calculated in a predetermined period is a predetermined value or larger.

In the second embodiment, the concentration judger 21 measures the presence of the P300 waveform being the event related potential by calculating the difference between the potential immediately after the high-frequency stimulus (the stimulus presenting content) is applied and the potential after the low-frequency stimulus (the concentration judging content) is applied; however, it is not limited thereto. For example, the concentration judger 21 may judge that a change corresponding to the P300 waveform occurs if the amplitude of the event related potential when the concentration judging content is present is a predetermined value or larger.

In the second embodiment, the example has been described in which the concentration judger 21 judges whether or not the user concentrates on the stimulus presenting content by the presence of the P300 waveform; however, it is not limited thereto. For example, the concentration judger 21 may judge the degree of concentration (a concentration level) in accordance with the magnitude of the amplitude of the P300 waveform. With this configuration, the scenario can be changed and the database can be updated even on the basis of the result of the concentration level. Accordingly, the mental state of the user can be further efficiently led to the target mental state. Alternatively, without limiting to the P300 waveform, judgment on concentration can be made if a change in event related potential, such as an N400 waveform, is measured. Alternatively, judgment on concentration can be made if a reaction, such as a body motion, occurs immediately after the concentration judging content is presented. That is, the concentration judger 21 may execute concentration judgment on the basis of at least one of the biological information such as a body motion, and the event related potential, such as the P300 waveform or N400 waveform.

In the second embodiment, if the concentration judger 21 judges that the user does not concentrate on the stimulus presenting content, the user model database 17 and the stimulus content database 18 may correct the data when the user does not concentrate. Accordingly, more correct data can be collected, and the mental state of the user can be further efficiently led to the target mental state.

In the second embodiment, the example has been described in which the content presenter 15 reproduces a sound if the concentration judger 21 judges that the user does not concentrate; however, it is not limited thereto. For example, the content presenter 15 may display a video that causes the user to concentrate, or a video indicative of that the user does not concentrate currently. Alternatively, a vibration may be applied to the user. At this time, the series of processing or part of the processing shown in FIG. 13 may be stopped temporarily or for a predetermined period.

In the second embodiment, the example has been described in which the concentration judger 21 judges whether or not the user concentrates on the stimulus presenting content on the basis of the brain activity information acquired by the biological information acquirer 11; however, it is not limited thereto. For example, the brain activity information acquired by the biological information acquirer 11 may include brain activity information indicative of an activity state of the brain of the user and biological information other than the brain activity information.

The biological information is information on, for example, the heart rate, respiration, brain wave, oxygen density, bloodstream, facial expression, body motion, etc., of the user.

The concentration judger 21 judges whether or not the user concentrates on the stimulus presenting content on the basis of at least one of the brain activity information and the biological information other than the brain activity information acquired by the biological information acquirer 11 after the presentation of the concentration judging content.

The respective embodiments of the present disclosure have been described in detail by a certain degree; however the disclosed contents of these embodiments can be modified partly in the configuration. Also, the combination and order of components in the respective embodiments can be changed without departing from the scope and idea of the present disclosure.

Figure 14:
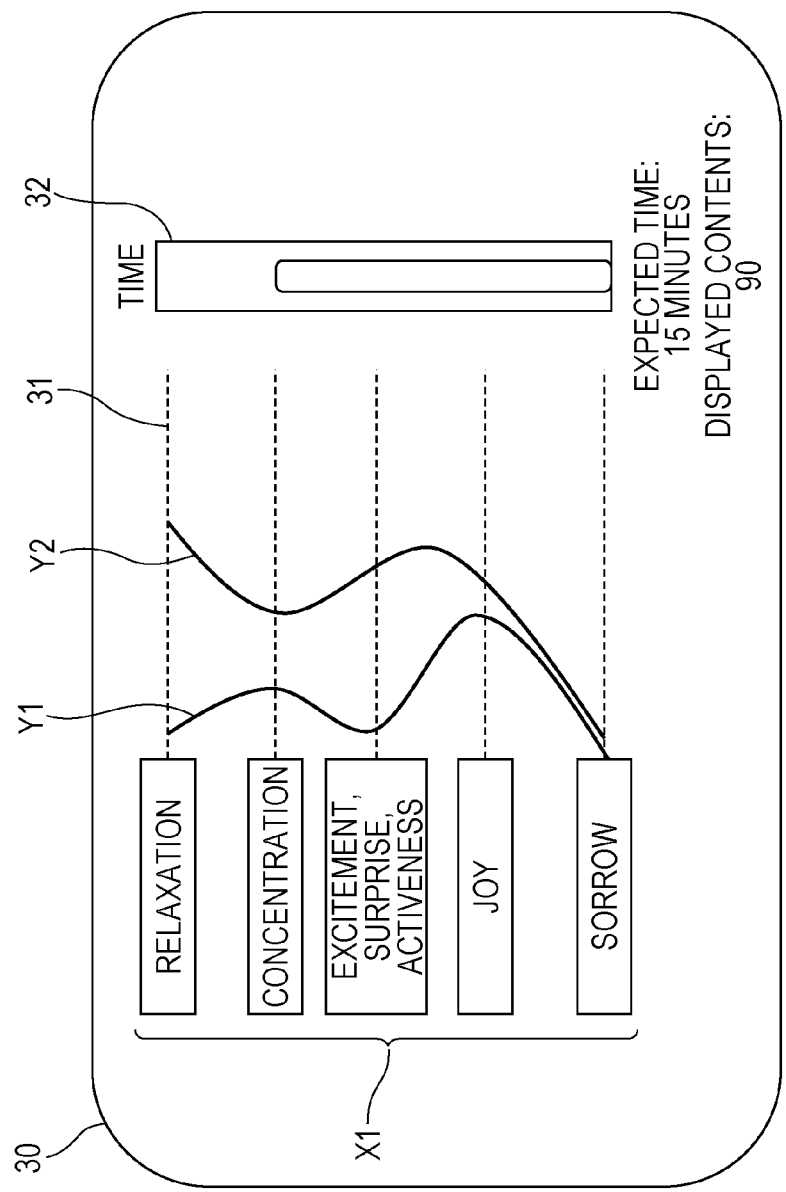
FIG. 14 illustrates an example of a target state setter according to any of the first and second embodiments of the present disclosure.

FIG. 14 illustrates a method of providing a screen 30 that sets the mental state the user aims at in any of the first and second embodiments. As shown in FIG. 14, a current estimated mental state Y1 of a user is displayed by sensing after the user is seated, for a mental state X1 including "relaxation," "concentration," "excitement, surprise, activeness," "joy," and "sorrow." A slide bar 31 is set for each of mental states of the mental state X1 for the estimated mental state Y1 of the user. The user can designate a target mental state Y2 by dragging or pointing with a pointer to the state as the target.

At this time, since the scenario creator 14 creates a scenario simultaneously, effects on the mental state by respective contents can be added, and the number of times of content presentation and the period of content presentation to attain the target mental state Y2 can be obtained. Accordingly, the user can select the target state while the required period is expected. Also, as shown in FIG. 14, a bar 32 may be displayed on the screen 30. The bar 32 indicates the number of times of content presentation or the period of content presentation.

Figure 15:
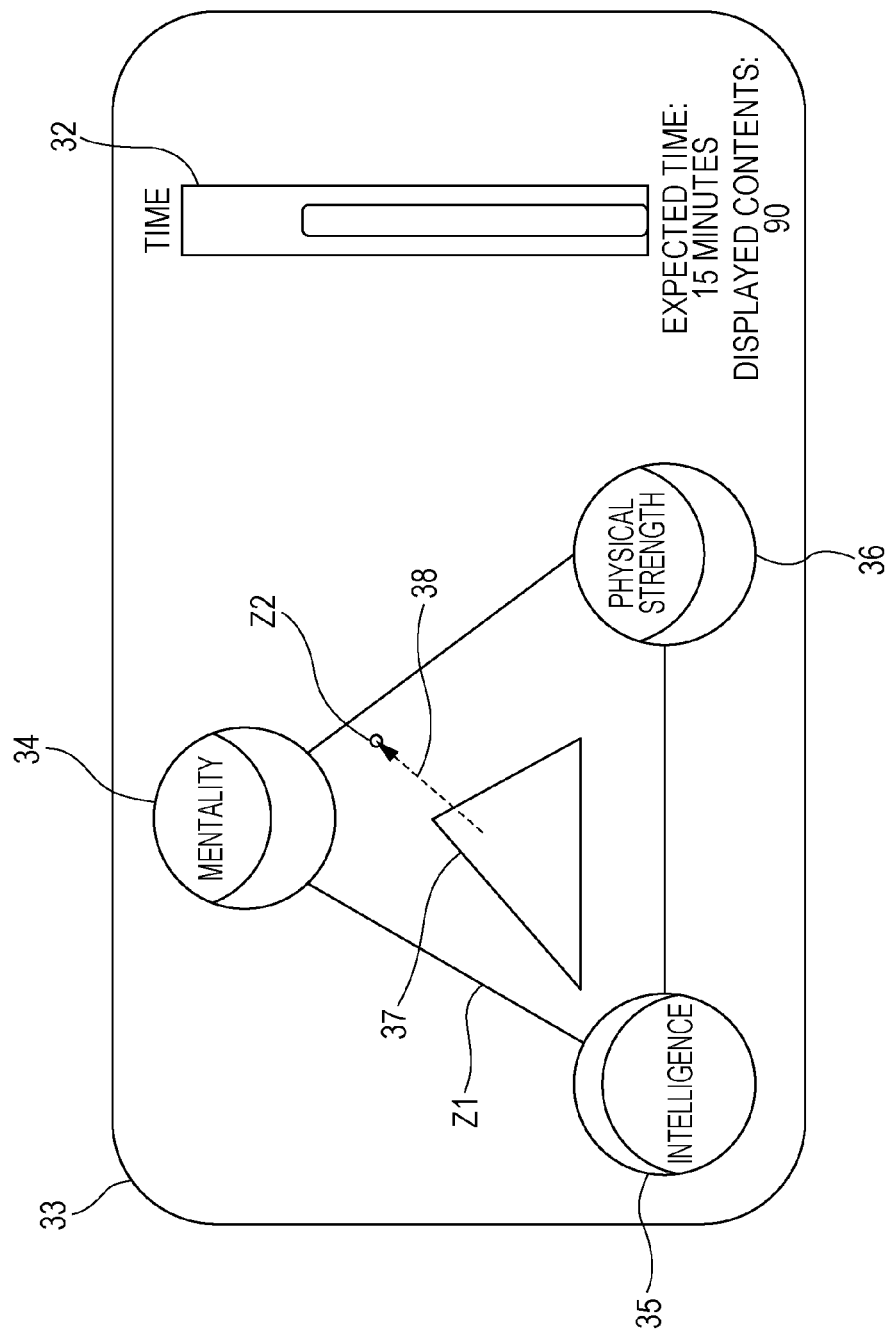
FIG. 15 illustrates another example of the target state setter according to any of the first and second embodiments of the present disclosure.

In any of the first and second embodiments, the mental states are defined as "relaxation," "concentration," "excitement, surprise, activeness," "joy," and "sorrow" shown in FIG. 3. However, the mental state is not limited thereto. For example, the mental state may be expressed in a diagram including "mentality," "physical strength," and "intelligence." The physical strength may be judged by using the body motion acquired by the pressure sensor. FIG. 15 illustrates an example of the target state setter 13, and illustrates a screen 33 when the user is seated. As shown in FIG. 15, in the stimulus presenting system according to the embodiment of the present disclosure, a mental state Z1 of the user estimated by the mental state estimator 12 may be displayed on the screen 33 in a diagram 37 with respect to three axes including "mentality" (reference sign 34 in FIG. 15), "intelligence" (reference sign 35 in FIG. 15), and "physical strength" (reference sign 36 in FIG. 15). The user may set a target mental state Z2 by dragging and dropping the diagram 37 displayed on the display screen 33 in a direction in which the mentality is increased (arrow 38 in FIG. 15) with a finger, and hence deforming the shape of the diagram 37. Alternatively, the mental state of the user may be expressed by converting "mentality," "intelligence," and "physical strength" into numerical values, and the amount of stimuli required to attain the target mental state can be displayed. At this time, the physical strength is not actually increased, but is mentally increased by presenting a content that urges the user to exercise with use of dance video or music. Also in the screen 33 in FIG. 15, the bar 32 indicative of the number of times of content presentation or the period of content presentation can be displayed similarly to the screen 30 in FIG. 14.

Figure 16:
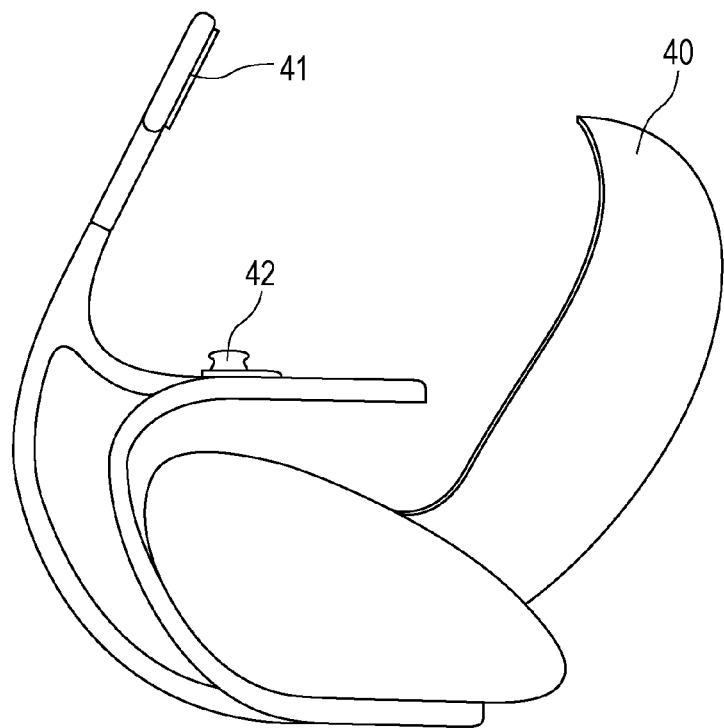
FIG. 16 is a side view of a chair to which the stimulus presenting system according to any of the first and second embodiments of the present disclosure is applied.
Figure 17:
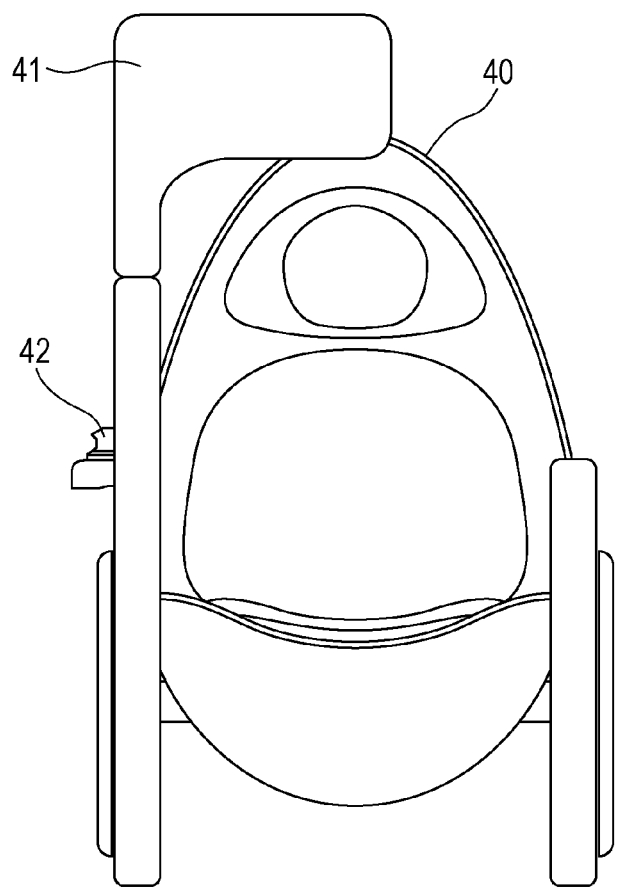
FIG. 17 is a front view of the chair to which the stimulus presenting system according to any of the first and second embodiments of the present disclosure is applied.

Also, FIGS. 16 and 17 illustrate a design of a chair 40 to which the stimulus presenting system according to any of the embodiments of the present disclosure is applied. FIG. 16 is a side view of the chair 40 to which the stimulus presenting system according to any of the embodiments of the present disclosure is applied. FIG. 17 is a front view of the chair 40 to which the stimulus presenting system according to any of the embodiments of the present disclosure is applied. A display 41 shown in FIGS. 16 and 17 serves as the display section of the content presenter 15 and the display section of the target state setter 13 in the stimulus presenting system according to any of the embodiments of the present disclosure. Also, an operation button 42 shown in FIGS. 16 and 17 corresponds to the input operation section of the target state setter 13 in the stimulus presenting system according to any of the embodiments of the present disclosure. As shown in FIGS. 16 and 17, since the display 41 integrally provided with the chair 40 is arranged, the user can watch the display at an optimal angle in a comfortable state while the backrest of the chair 40 is tilted and part of the weight of the head is put on the chair 40. Accordingly, the brain wave and biological information can be more correctly measured. Also, the operation button 42 is arranged at the chair 40. The user can set the target mental state etc. by operating the operation button 42.

The biological information acquirer 11 may be attached to the chair 40 shown in FIGS. 16 and 17.

Also, the mental state estimator 12, the scenario creator 14, the mental state determiner 16, the effect difference calculator 19, and the concentration judger 21 may be attached to the chair 40 shown in FIGS. 16 and 17.

For example, the computer with the mental state estimator 12, the scenario creator 14, the mental state determiner 16, the effect difference calculator 19, and the concentration judger 21 installed therein may be attached to the chair 40.

Alternatively, the computer may be arranged at a position different from the position at which the chair 40 is arranged. Still alternatively, the computer may be a server apparatus connected to the chair 40 through a communication network. The communication network includes one or both of a wired network and a wireless network.

Also, the user model database 17 and the stimulus content database 18 may be attached to the chair 40 shown in FIGS. 16 and 17. For example, the user model database 17 and the stimulus content database 18 may be installed in the computer, or may be configured as apparatuses physically independent from the computer and connected to the computer.

In the example shown in FIGS. 16 and 17, the example has been described in which the respective components of the stimulus presenting system according to any of the embodiments of the present disclosure are attached to the chair 40; however, it is not limited thereto.

For example, the respective components of the stimulus presenting system according to any of the embodiments of the present disclosure may be attached to an object with a shape on which a user can sit, such as a chair, a sofa, or a seat of a toilet; a seat of a vehicle, a seat of a train, or a seat of an airplane; a bed; etc.

The present disclosure is useful for a stimulus presenting system, a stimulus presenting method, a computer, and a control method.

Also, the stimulus presenting system according to any of the embodiments of the present disclosure can be applied to an object with a shape on which a user can sit, such as a chair, a sofa, or a seat of a toilet; a seat of a vehicle, a seat of a train, or a seat of an airplane; a bed; etc.; for the purpose of leading the mental state of a user to a target state.

What is claimed is:
1. A stimulus presenting system that leads a mental state of a user to a target mental state, the system comprising:
   a biological information acquirer that acquires biological information on the user, wherein the biological information acquirer includes a sensor;
   a mental state estimator that estimates the mental state of the user on the basis of the biological information acquired by the biological information acquirer;
   a target state setter that sets a target mental state indicative of a mental state the user aims at, after the mental state estimator estimates that the mental state of the user is a first mental state;
   a user model database that stores a user model;
   a scenario creator that creates a scenario in accordance with the user model, the scenario including at least one stimulus presenting content which gives an influence on the mental state of the user on the basis of the set target mental state;
   a content presenter that presents the at least one stimulus presenting content on the basis of the created scenario, wherein the content presenter includes a display or a speaker;
   a mental state determiner that determines whether or not a second mental state which is a mental state of the user estimated by the mental state estimator on the basis of biological information on the user acquired after the presentation of the stimulus presenting content is started attains the set target mental state; and
   an effect difference calculator that calculates a difference between a first change amount indicative of a change amount of the mental state of the user caused by the presentation of the stimulus presenting content and estimated by the mental state estimator, and a second change amount indicative of a change amount of the mental state of the user caused by the presentation of the stimulus presenting content and expected on the basis of the created scenario,
   wherein, if the difference calculated by the effect difference calculator is a predetermined value or larger, the scenario creator changes the scenario and updates the user model to reflect the changes to the scenario for correction such that the changed scenario is set to be presented for the target metal state, and
   wherein at least one of the mental state estimator, the scenario creator, the mental state determiner and the effect difference calculator includes a processor.

2. The stimulus presenting system according to claim 1, wherein, if the mental state determiner determines that the second mental state attains the target mental state, the content presenter ends the presentation of the stimulus presenting content.

3. The stimulus presenting system according to claim 1, wherein the target state setter sets the target mental state on the basis of input data relating to a target mental state input by an input operation by the user.

4. The stimulus presenting system according to claim 1, further comprising:
   a storage medium that stores a target mental state set in past as history information,
   wherein the target state setter sets the target mental state on the basis of the history information stored in the storage medium.

5. The stimulus presenting system according to claim 1, wherein the user model defines a tendency of a change in the mental state of the user caused by the presentation of the stimulus presenting content in association with the user,
   wherein the stimulus presenting system further comprises a stimulus content database that stores an expected change amount indicative of a change amount of the mental state of the user expected in reaction to the presentation of the stimulus presenting content, and wherein the scenario creator creates the scenario on the basis of at least one of data in the user model database and data in the stimulus content database.

6. The stimulus presenting system according to claim 5, wherein the effect difference calculator calculates the difference between the first change amount indicative of the change amount of the mental state of the user caused by the presentation of the stimulus presenting content and estimated by the mental state estimator, and the second change amount indicative of the change amount of the mental state of the user caused by the presentation of the stimulus presenting content and expected on the basis of the at least one of the data in the user model database and the data in the stimulus content database.

7. The stimulus presenting system according to claim 6, wherein, if the difference is the predetermined value or larger, the effect difference calculator updates the at least one of the data in the user model database and the data in the stimulus content database.

8. The stimulus presenting system according to claim 6, further comprising:
a concentration judger that judges whether or not the user concentrates on the stimulus presenting content if the difference calculated by the effect difference calculator is the predetermined value or larger,
wherein, if the concentration judger judges that the user does not concentrate on the stimulus presenting content, the difference calculated by the effect difference calculator is corrected.

9. The stimulus presenting system according to claim 8, wherein the biological information acquired by the biological information acquirer includes brain activity information indicative of an activity state of the brain of the user and biological information other than the brain activity information,
wherein the content presenter further presents concentration judging content to judge whether or not the user concentrates on the stimulus presenting content, and
wherein the concentration judger judges whether or not the user concentrates on the stimulus presenting content on the basis of at least one of the brain activity information and the biological information other than the brain activity information acquired by the biological information acquirer after the presentation of the concentration judging content.

10. The stimulus presenting system according to claim 9, wherein the concentration judger compares first brain activity information included in biological information acquired in a period after the presentation of the concentration judging content and before presentation of next content with second brain activity information included in biological information acquired during presentation of stimulus presenting content other than the concentration judging content, judges that the user concentrates if a difference between the first brain activity information and the second brain activity information is a predetermined amount or more, and judges that the user does not concentrate otherwise.

11. The stimulus presenting system according to claim 9, wherein the stimulus content database holds attribute information in which the stimulus presenting content is classified on the basis of at least one of a type of content and an effect given to the mental state of the user,
wherein the scenario creator creates a scenario including the stimulus presenting content and the concentration judging content on the basis of the attribute information held in the stimulus content database, and
wherein the concentration judging content includes content having attribute information different from the attribute information on the stimulus presenting content.

12. The stimulus presenting system according to claim 11, wherein the scenario creator creates a scenario that presents the concentration judging content with a lower frequency than a frequency with which the stimulus presenting content is presented.

13. The stimulus presenting system according to claim 11, wherein the scenario creator judges a number of pieces of attribute information being same as at least one piece of attribute information owned by content presented previously to the presentation of the concentration judging content and a similarity of attribute information on the basis of the attribute information held in the stimulus content database, and selects content with lowest similarity as the concentration judging content.

14. The stimulus presenting system according to claim 8, wherein, if the concentration judger judges that the user does not concentrate on the stimulus presenting content, the content presenter generates a sound.

15. A stimulus presenting method that leads a mental state of a user to a target mental state, the method comprising:
acquiring, using a sensor, biological information on the user;
estimating, using a processor, the mental state of the user on the basis of the biological information;
setting, using the processor, a target mental state indicative of a mental state the user aims at, after it is estimated that the mental state of the user is a first mental state;
storing, in a user model database, a user model;
creating, using the processor, a scenario in accordance with the user model, the scenario including at least one stimulus presenting content which gives an influence on the mental state of the user on the basis of the set target mental state;
presenting, using a display or a speaker, the at least one stimulus presenting content on the basis of the created scenario;
determining, using the processor, whether or not a second mental state which is an estimated mental state of the user on the basis of biological information on the user acquired after the presentation of the stimulus presenting content is started attains the target mental state;
calculating, using the processor, a difference between a first change amount indicative of a change amount of the mental state of the user caused by the presentation of the stimulus presenting content and estimated in the mental state estimation, and a second change amount indicative of a change amount of the mental state of the user caused by the presentation of the stimulus presenting content and expected on the basis of the created scenario;
changing, using the processor, the scenario if the difference calculated in the effect difference calculation is a predetermined value or larger; and
updating, using the processor, the user model to reflect the changes to the scenario for correction such that the changed scenario is set to be presented for the target metal state.

16. The stimulus presenting method according to claim 15, wherein, if the mental state determination determines that the second mental state attains the target mental state, the presentation of the stimulus presenting content is ended.

17. The stimulus presenting method according to claim 15, wherein the target state setting includes setting the target mental state on the basis of input data relating to a target mental state input by an input operation by the user.

18. The stimulus presenting method according to claim 15, wherein the target state setting sets the target mental state on the basis of history information on a target mental state set in past and stored in a storage medium.

19. The stimulus presenting method according to claim 15, wherein the scenario creation further creates the scenario on the basis of at least one of data in the user model database that stores the user model, the user model defining a tendency of a change in the mental state of the user caused by the presentation of the stimulus presenting content in association with the user, and data in a stimulus content database that stores an expected change amount indicative of a change amount of the mental state of the user expected in reaction to the presentation of the stimulus presenting content.

20. The stimulus presenting method according to claim 19,
wherein, the calculating calculates the difference between the first change amount indicative of the change amount of the mental state of the user caused by the presentation of the stimulus presenting content and estimated in the mental state estimation, and the second change amount indicative of the change amount of the mental state of the user caused by the presentation of the stimulus presenting content and expected on the basis of the at least one of the data in the user model database and the data in the stimulus content database.

21. The stimulus presenting method according to claim 20, further comprising updating the at least one of the data in the user model database and the data in the stimulus content database if the difference calculated in the effect difference calculation is the predetermined value or larger.

22. The stimulus presenting method according to claim 21, further comprising:
judging whether or not the user concentrates on the stimulus presenting content if the difference calculated in the effect difference calculation is the predetermined value or larger,
wherein, if the concentration judgment judges that the user does not concentrate on the stimulus presenting content, the concentration judgment includes correcting the difference calculated in the effect difference calculation.

23. The stimulus presenting method according to claim 22,
wherein the biological information acquired in the biological information acquisition includes brain activity information indicative of an activity state of the brain of the user and biological information other than the brain activity information,
wherein the content presentation further presents concentration judging content to judge whether or not the user concentrates on the stimulus presenting content, and
wherein the concentration judgment judges whether or not the user concentrates on the stimulus presenting content on the basis of at least one of the brain activity information and the biological information other than the brain activity information acquired in the biological information acquisition after the presentation of the concentration judging content.

24. The stimulus presenting method according to claim 23, wherein the concentration judgment compares first brain activity information included in biological information acquired in a period after the presentation of the concentration judging content and before presentation of next stimulus presenting content with second brain activity information included in biological information acquired during presentation of content other than the concentration judging content, judges that the user concentrates if a difference between the first brain activity information and the second brain activity information is a predetermined amount or more, and judges that the user does not concentrate otherwise.

25. The stimulus presenting method according to claim 23, further comprising:
changing the scenario created in the scenario creation into a scenario including the stimulus presenting content and the concentration judging content on the basis of attribute information in which the stimulus presenting content held in the stimulus content database is classified on the basis of at least one of a type of content and an effect given to the mental state of the user,
wherein the concentration judging content includes content having attribute information different from the attribute information on the stimulus presenting content.

26. The stimulus presenting method according to claim 25, wherein the scenario changing changes the scenario to a scenario that presents the concentration judging content with a lower frequency than a frequency with which the stimulus presenting content is presented.

27. The stimulus presenting method according to claim 25, wherein the scenario changing judges a number of pieces of attribute information being same as at least one piece of attribute information owned by content presented previously to the presentation of the concentration judging content and a similarity of attribute information on the basis of the attribute information held in the stimulus content database, and selects content with lowest similarity as the concentration judging content.

28. The stimulus presenting method according to claim 22, further comprising generating a sound if the concentration judgment judges that the user does not concentrate on the stimulus presenting content.

29. A computer included in a stimulus presenting system that leads a mental state of a user to a target mental state, the computer comprising:
a mental state estimator that estimates the mental state of the user on the basis of biological information acquired by a biological information acquiring device connected to the computer;
a processor that acquires, from a user model database, a user model;
a scenario creator that creates a scenario in accordance with the user model, the scenario including at least one stimulus presenting content which gives an influence on the mental state of the user on the basis of a target mental state indicative of a mental state the user aims at set by a target state setting device connected to the computer after the mental state estimator estimates that the mental state of the user is a first mental state, and transmits the created scenario to a content presenting device connected to the computer;
a mental state determiner that determines whether or not a second mental state which is a mental state of the user estimated by the mental state estimator on the basis of biological information on the user acquired after a presentation of the stimulus presenting content by the content presenting device is started attains the set target mental state; and an effect difference calculator that calculates a difference between a first change amount indicative of a change amount of the mental state of the user caused by the presentation of the stimulus presenting content and estimated by the mental state estimator, and a second change amount indicative of a change amount of the mental state of the user caused by the presentation of the stimulus presenting content and expected on the basis of the created scenario, wherein, if the difference calculated by the effect difference calculator is a predetermined value or larger, the scenario creator changes the scenario and updates the user model to reflect the changes to the scenario for correction such that the changed scenario is set to be presented for the target metal state, and wherein, at least one of the mental state estimator, the scenario creator, the mental state determiner and the effect difference calculator includes the processor.

30. A control method of a computer included in a stimulus presenting system that leads a mental state of a user to a target mental state, the method comprising:

estimating, using a processor of the computer, the mental state of the user on the basis of biological information acquired by a biological information acquiring device connected to the computer;

acquiring, using the processor and from a user model database, a user model;

creating, using the processor, a scenario in accordance with the user model, the scenario including at least one stimulus presenting content which gives an influence on the mental state of the user on the basis of a target mental state indicative of a mental state the user aims at set by a target state setting device connected to the computer after the mental state estimation estimates that the mental state of the user is a first mental state, and transmits the created scenario to a content presenting device connected to the computer;

determining, using the processor, whether or not a second mental state which is a mental state of the user estimated in the mental state estimation on the basis of biological information on the user acquired after a presentation of the stimulus presenting content by the content presenting device is started attains the set target mental state;

calculating, using the processor, a difference between a first change amount indicative of a change amount of the mental state of the user caused by the presentation of the stimulus presenting content and estimated in the mental state estimation, and a second change amount indicative of a change amount of the mental state of the user caused by the presentation of the stimulus presenting content and expected on the basis of the created scenario;

changing, using the processor, the scenario if the difference calculated in the effect difference calculation is a predetermined value or larger; and updating, using the processor, the user model to reflect the changes to the scenario for correction such that the changed scenario is set to be presented for the target metal state.

* * * * *